United States Patent [19]
Weiner

[11] Patent Number: 5,851,759
[45] Date of Patent: Dec. 22, 1998

[54] HETERODUPLEX TRACKING ASSAY (HTA) FOR GENOTYPING HCV

[75] Inventor: Amy J. Weiner, Benicia, Calif.

[73] Assignee: Chiron Corporation, Emeryville, Calif.

[21] Appl. No.: 634,797

[22] Filed: Apr. 19, 1996

[51] Int. Cl.⁶ .............................. C12Q 1/70; C12Q 1/68; C12P 19/34; G07H 21/04
[52] U.S. Cl. ................................ 435/5; 435/6; 435/91.2; 435/91.51; 536/24.33; 935/8; 935/99; 935/98
[58] Field of Search .......................... 435/4, 6, 91.1–91.2, 435/91.5, 5, 91.51; 536/23.72, 24.3–24.33; 935/8, 77, 78

[56] References Cited

U.S. PATENT DOCUMENTS

| | | | |
|---|---|---|---|
| 5,427,909 | 6/1995 | Okamoto et al. | 435/54 |
| 5,437,974 | 8/1995 | Ryan et al. | 435/5 |
| 5,514,539 | 5/1996 | Bukh et al. | 435/5 |
| 5,712,088 | 1/1998 | Houghton et al. | 435/5 |
| 5,714,596 | 2/1998 | Houghton et al. | 536/23.72 |

FOREIGN PATENT DOCUMENTS

0 318 216-A1  5/1989  European Pat. Off. .
0 388 232-A1  9/1990  European Pat. Off. .

OTHER PUBLICATIONS

Bukh et al., *Proc. Natl. Acad. Sci. (USA)* (1993) 90:8234–38.
Choo et al., *Proc. Natl. Acad. Sci. (USA)* (1991) 88:2451–55.
Choo et al., *Science* (1989) 244:359–362.
Davidson et al., *J. of General Virology* (1995) 76:1197–1204.
Delwart et al., *Heteroduplex Mobility Analysis Protocol Version 3* pp. 1–15.
Delwart et al., *Science* (1993) 262:1257–61.
Delwart et al., *J. of Virology* (1994) 68(10):6672–83.
Delwart et al., *Cold Spring Harbor Laboratory* (1995) "Genetic Subtyping of Human Immunodeficiency Virus Using a Heteroduplex Mobility Assay" (Manual Supplement) pp. S202–S216.
Houghton et al., *Hepatology* (1991) 14(2):381–388.
Kostrikis et al., *J. of Virology* (1995) 69(10):6122–30.
Kostrikis et al., *J. of Virology* (1996) 70(1):445–458.
Kuo et al., *Science* (1989) 244:362–364.
Moore et al., *J. of Virology* (1996) 70(1):427–444.
Okamoto et al., *Virology* (1992) 188:331–341.
Okamoto et al., *J. of General Virology* (1992) 73:673–679.
Wilson et al., *J. of General Virology* (1995) 76:1–9.
Yoshioka et al., *Hepathology* (1992) 16(2):293–299.
Kato et al., *Proc. Natl. Acad. Sci. (USA)* (1990) 87:9524–2528.
Sakamoto et al., *J. Gen. Virol.* (1994) 75:1761–1768.
Cammarota et al., *J. Clin. Microb.* (1995) 33:2781–2784.
Shimizu et al., *Proc. Natl. Acad. Sci. (USA)* (1992) 77:5477–5481.
Saiki in PCR Technology: Principles and Applications for DNA amplification edited by Erlica Stockton Press, New York pp. 7–15, 1989.
van Doorn et al. (1 Jun. 1995) GenBank No. L39312, 1995.
Okamoto et al (12 Aug. 1995) GenBank No. D10077, 1995.
Viazov et al. J. Virol. Methods. 48:81–92 (Jun. 1994).
Widerl et al. J. Med. Virol. 44:272–279 (Nov. 1994).
Pozzato et al. J. Med. Virol. 45:445–450 (Apr. 1995).

*Primary Examiner*—Stephanie W. Zitomer
*Assistant Examiner*—Debra Shoemaker
*Attorney, Agent, or Firm*—Robins & Associates; Alisa A. Harbin; Robert P. Blackburn

[57] ABSTRACT

A heteroduplex tracking assay (HTA), a hybridization based method of determining the genetic relationship between two or more viral genomes, for genotyping HCV is disclosed. The HTA for genotyping HCV was developed using single stranded probes derived form the carboxyl terminus of core and part of the E1 for HCV subtypes 1a, 1b, 2a, 2b, and 3a. HTA is more accurate than RFLP for sub-typing HCV and has potential for identifying new variants and is useful for epidemiological studies.

23 Claims, 14 Drawing Sheets

```
HTA1    AACTCAAGCATTGTGTATGAAGCGGCGGACATGATCATGCACACCCCCGGGTGCGTGCCA
HTA2    AACTCAAGCATCGTGTATGAGGCAGCGGAAGTGATCATGCACATTCCCGGGTGCGTGCCC
HTA4    AACTCAAGCATAGTATATGAGGCAGCGGACATAATCATGCATACCCCCGGGTGCGTGCCC
HTA24   AACACGAGCATTGTGTATGAGGCAGCGGACTTGATCATGCACGTCCCCGGGTGCGTGCCC
HTA28   AACTCAAGCATCGTGTATGAGGCGGCGGAAGTGATCATGCACATTCCTGGGTGCGTGCCC
HCV-1   AACTCGAGTATTGTGTACGAGGCGGCCGATGCCATCCTGCACACTCCGGGTGCGTCCCT
HCV-J   AACTCAAGTATTGTGTATGAGGCAGCGGACATGATCATGCACACCCCCGGGTGCGTGCCC
HC-J6   AATGATAGCATTACCTGGCAACTCCAGGCTGCTGTCCTCCACGTCCCCGGGTGCGTCCCG
HC-J8   AACAACAGCATCACCTGGCAGCTCACTGACGCAGTTCTCCATCTTCCTGGATGCGTCCCA
NZL-1   AATAGCAGTATTGTGTATGAGGCCGATGATGTCATTCTGCACACACCCGGCTGTGTACCT

HTA1    TGCGTCCGGGAGGGCAATCTCTCCCGCTGCTGGGTAGCGCTCACTCCCACGCTCGCGGCC
HTA2    TGCGTTCGGGAGAGCAATCTCTCCCGCTGCTGGGTAGCGCTCACCCCCACACTCGCGGCC
HTA4    TGTGTTCGGGAGGTCAACTCCTCCCGCTGCTGGGCAGCGCTCACCCCTACGCTCGCGGCC
HTA24   TGCGTTCGGGAGGGCAACTCCTCCCGATGCTGGGTAGCGCTCACTCCCACGATCGCGGCC
HTA28   TGCGTTCGGGAGGGCGACTTCTCCCGCTGCTGGGTAGCGCTCACCCCCACACTCGCGGCC
HCV-1   TGCGTTCGTGAGGGCAACGCCTCGAGGTGTTGGGTGGCGATGACCCCTACGGTGGCCACC
HCV-J   TGCGTCCGGGAGAGTAATTTCTCCCGTTGCTGGGTAGCGCTCACTCCCACGCTCGCGGCC
HC-J6   TGCGAGAAAGTGGGGAATACATCTCGGTGCTGGATACCGGTCTCACCGAATGTGGCCGTG
HC-J8   TGTGAGAATGATAATGGCACCTTGCATTGCTGGATACAAGTAACACCCAACGTGGCTGTG
NZL-1   TGTGTCCAGGACGGCAATACATCTACGTGCTGGACCCCAGTGACACCTACAGTGGCAGTC
JK1a    TGTGTTCGCGAGGGCAACGCCTCGAGGTGTTGGGTGGCGATGACCCCTACGGTGGCCACC

HTA1    AGAAACAGCAGCGTTCCTACTACGACAATACGACGCCATGTCGACTTGCTAGTAGGAGCG
HTA2    AGGAACAGCAGCGTCCCCACCACGACAATACGACGCCACGTCGACTTGCTCGTTGGGGCG
HTA4    AGGAACTCCAGCGTGCCCACTACGACAATACGACGCCACGTCGACTTGCTCGTTGGGGCG
HTA24   AGGAACAGCAGTGTCCCCGTTACGACCATACGACGCCACGTCGATTTGCTCGTTGGGGCG
HTA28   AGGAATAACAGCGTCCCCACTACGACAATACGACGCCACGTCGACTTGCTCGTTGGGGCG
HCV-1   AGGGATGGCAAACTCCCCGCGACGCAGCTTCGACGTCACATCGATCTGCTTGTCGGGAGC
HCV-J   AGGAACAGCAGCATCCCCACCACGACAATACGACGCCACGTCGATTTGCTCGTTGGGGCG
HC-J6   CAGCAGCCCGGCGCCCTCACGCAGGGCTTACGGACGCACATTGACATGGTTGTGATGTCC
HC-J8   AAACACCGCGGTGCGCTCACTCGTAGCCTGCGAACACACGTCGACATGATCGTAATGGCA
NZL-1   AGGTACGTCGGAGCAACTACTGCTTCGATACGCAGTCATGTGGACCTATTAGTAGGCGCG

HTA1    GCTGCTTTTTGCTCCGCCATGTACGTGGGGGACCTCTGCGGATCTATTTTCCTCGTCTCC
HTA2    GCTGCCTTCTGCTCCGCTATGTATGTGGGGGATCTCTGCGGATCTGTTTTCCTTGTCTCC
HTA4    GCTGCTTTCTGCTCCGCTATGTACGTGGGGGATCTATGCGGATCTGTTCTACTTGTCTCT
HTA24   GCTGCTCTTTGCTCCGCCATGTACGTGGGGGATCTCTGCGGATCTGTCTTCCTCGCTTCC
HTA28   GCTGCCTTCTGCTCCGCTATGTACGTGGGGGATCTCTGCGGATCTGTTTTCCTTGTCTCC
HCV-1   GCCACCCTCTGTTCGGCCCTCTACGTGGGGGACCTATGCGGGTCTGTCTTTCTTGTCGGC
HCV-J   GCTGCTCTGTTCCGCTATGTTGGGGATCTCTGCGGATCCGTTTTTCTCGTCTCC
HC-J6   GCCACGCTCTCCGCTCTTTACGTGGGGGACCTCTGCGGTGGGGTGATGCTTGCAGCC
HC-J8   GCTACGGCCTGCTCGGCCTTGTATGTGGGAGATGTGTGCGGGGCCGTGATGATTCTATCG
NZL-1   GCCACGATGTGCTCTGCGCTCTACGTGGGTGATATGTGTGGGGCTGTCTTTCTCGTGGGA

HTA1    CAACTGTTCACCTTCTCGCCCCGCCGGCATCATACAGTACAGGACTGCAATTGCTCGATC
HTA2    CAACTGTTCACCTTTTCGCCTCGCCGGCATGAGACAGTACAGGACTGCAATTGTTCAATC
HTA4    CAGCTGTTCACCTTCTCACCTCGCCGGCACGAGACAGTGCAGGACTGCAATTGTTCAATC
HTA24   CAGTTGTTCACTTTCTCGCCTCGCCAGCATCAGACGGTACAGGACTGCAACTGCTCAATC
HTA28   CAACTGTTCACCTTTTCGCCTCGCCGGCATGCGACAGTACAGGACTGCAATTGTTCAATC
```

FIG. 3A-1

| | |
|---|---|
| HCV-1 | CAACTGTTCACCTTCTCTCCCAGGCGCCACTGGACGACGCAAGGTTGCAATTGCTCTATC |
| HCV-J | CAGCTGTTCACCTTCTCACCTCGCCGGTATGAGACGGTACAAGATTGCAATTGCTCAATC |
| HC-J6 | CAGATGTTCATTGTCTCGCCACAGCACCACTGGTTTGTGCAAGACTGCAATTGCTCCATC |
| HC-J8 | CAGGCTTTCATGGTATCACCACAACGCCACAACTTCACCCAAGAGTGCAACTGTTCCATC |
| NZL-1 | CAAGCCTTCACGTTCAGACCTCGACGCCATCAAACGGTCCAGACCTGTAACTGCTCGCTG |

| | |
|---|---|
| HTA1 | TATCCC |
| HTA2 | TATCCC |
| HTA4 | TATCCC |
| HTA24 | TATCCC |
| HTA28 | TATCCC |
| HCV-1 | TATCCC |
| HCV-J | TATCCC |
| HC-J6 | TACCCT |
| HC-J8 | TACCAA |
| NZL-1 | TACCCA |

FIG. 3A-2

```
JK1a      CGCAACTCCACGGGGCTTTACCACGTCACCAATGATTGCCCTAACTCGAGTATTGTGTAC
JK2a      AAGAACACCAGCGACAGCTACATGGTGACCAATGACTGCCAAAATGACAGCATCACCTGG
JK2b      AGGAACATCAGTTCTAGCTACTACGCCACTAATGACTGCTCGAACAACAGCATCACCTGG
SW83.2c   AAGGACACCGGCGACTCCTACATGCCGACCAACGATTGCTCCAACTCTAGTATCGTTTGG
HTA23     AAAAACACCAGCATCTCCTATATGGCGACCAACGACTGCTCCAATTCCAGCATCGCTTGG
HTA33     AAGAACACCAGCGACTCCTACATGGCGACTAACGACTGCTCTAACTCCAGCATCGTTTGG
HTA30     AAGAACACCAGCACCTCCTACATGGTGACTAACGATTGCTCCAACTCCAGCATCGTTTGG
HCV-1     CGCAACTCCACGGGGCTTTACCACGTCACCAATGATTGCCCTAACTCGAGTATTGTGTAC
HCV-J     CGCAACGTGTCCGGGATATACCATGTCACGAACGACTGCTCCAACTCAAGTATTGTGTAT
HC-J8     AGGAACATTAGTTCTAGCTACTACGCCACTAATGATTGCTCAAACAACAGCATCACCTGG
NZL-1     CGGAATACGTCTGGCCTCTACGTCCTTACCAACGACTGTTCCAATAGCAGTATTGTGTAT
HC-J6     AAGAACATCAGTACCGGCTACATGGTGACCAACGACTGCACCAATGATAGCATTACCTGG
                *           **       ** ** ** **         **        ** **        *

JK1a      GAGACGGCCGATGCCATCCTGCACACTCCGGGGTGCGTCCCTTGTGTTCGCGAGGGCAAC
JK2a      CAGCTTGAGGCTGCGGTCCTCCACGTCCCCGGGTGCGTCCCGTGCGAGAGAGTGGGAAAT
JK2b      CAGCTCACCAACGCAGTTCTCCACCTTCCCGGATGCGTCCCATGTGAGAATAATAATGGC
SW83.2c   CAGCTTGAAGGAGCAGTGCTTCATACTCCTGGATGCGTCCCTTGTGAGCGTACCGCCAAC
HTA23     CAGTTTGACGGCGCAGTGCTCCATACTCCTGGATGTGTCCCTTGCGAACGGACCGGCAAC
HTA33     CAGCTTGAGGACGCAGTGCTCCATGTCCCTGGATGTGTCCCTTGTGAGAAGACTGGCAAT
HTA30     CAACTTGAAGGCGCAGTGCTCCATGTTCCTGGATGTGTCCCTTGTGAGCAGATCGGCAAC
HCV-1     GAGGCGGCCGATGCCATCCTGCACACTCCGGGGTGCGTCCCTTGCGTTCGTGAGGGCAAC
HCV-J     GAGGCAGCGGACATGATCATGCACACCCCGGGTGCGTGCCCTGCGTCCGGGAGAGTAAT
HC-J8     CAGCTCACTGACGCAGTTCTCCATCTTCCTGGATGCGTCCCATGTGAGAATGATAATGGC
NZL-1     GAGGCCGATGATGTCATTCTGCACACACCCGGCTGTGTACCTTGTGTCCAGGACGGCAAT
HC-J6     CAACTCCAGGCTGCTGTCCTCCACGTCCCCGGGTGCGTCCCGTGCGAGAAAGTGGGGAAT
                *           *    * **      ** **  ** ** ** ** ** *

JK1a      GCCTCGAGGTGTTGGGTGGCGATGACCCCTACGGTGGCCACCAGGGATGGCAAACTCCCC
JK2a      ACATCTCGGTGCTGGATACCGGTCTCACCAAACGTGGCTGTGCGGCAGCCCGGCGCCCTC
JK2b      ACCTTGCATTGCTGGATACAAGTAACACCTAATGTGGCCGTAAAACATCGCGGCGCACTC
SW83.2c   GTCTCTCGATGTTGGGTGCCGGTTGCCCCCAATCTCGCCATAAGTCAACCTGGCGCTCTC
HTA23     GCGTCCCGGTGTTGGGTGCCGGTTGCCCCCAATGTGGCTATAAGACAACCCGGCGCCCTC
HTA33     ACGTCTCGGTGCTGGGTGCCGGTTACCCCCAATGTGGCTACAAGTCAACCCGGCGCTCTC
HTA30     GTGTCTCAGTGTTGGGTGCCGGTTACCCCCAATATGGCCATAAGTACACCCGGCGCTCTC
HCV-1     GCCTCGAGGTGTTGGGTGGCGATGACCCCTACGGTGGCCACCAGGGATGGCAAACTCCCC
HCV-J     TTCTCCCGTTGCTGGGTAGCGCTCACTCCCACGCTCGCGGCCAGGAACAGCAGCATCCCC
HC-J8     ACCTTGCATTGCTGGATACAAGTAACACCCAACGTGGCTGTGAAACACCGCGGTGCGCTC
NZL-1     ACATCTACGTGCTGGACCCCAGTGACACCTACAGTGGCAGTCAGGTACGTCGGAGCAACT
HC-J6     ACATCTCGGTGCTGGATACCGGTCTCACCGAATGTGGCCGTGCAGCAGCCCGGCGCCCTC
                *    ** ***       *    * **  *    * **

JK1a      GCGACGCAGCTTCGACGTCACATCGATCTGCTTGTCGGGAGCGCCACCCTCTGTTCGGCC
JK2a      ACGCAGGGCTTGCGGACGCACATCGACATGATTGTGATGTCCGCCACGCTCTGCTCCGCT
JK2b      ACTCACAACCTGCGGACACATGTCGACATGATCGTAATGGCAGCTACGGTCTGTTCGGCC
SW83.2c   ACTAAGGGCCTGCGAGCACACATCGATATCATCGTGATGTCTGCTACGGTCTGTTCTGCC
HTA23     ACTAAGGGCATACGAACGCACATTGATGTCATCGTAATGTCTGCTACGCTCTGTTCTGCC
HTA33     ACCAGGGGCTTGCGGACGCACATCGATGTCATCGTGATGTCAGCCACGCTCTGCTCCGCT
HTA30     ACTAAGGGCTTGCGAACGCACATCGACGGCATCGTGATGTCCGCTACGCTCTGTTCCGCC
HCV-1     GCGACGCAGCTTCGACGTCACATCGATCTGCTTGTCGGGAGCGCCACCCTCTGTTCGGCC
HCV-J     ACCACGACAATACGACGCCACGTCGATTTGCTCGTTGGGCGGCTGCTCTCTGTTCCGCT
HC-J8     ACTCGTAGCCTGCGAACACACGTCGACATGATCGTAATGGCAGCTACGGCCTGCTCGGCC
NZL-1     ACTGCTTCGATACGCAGTCATGTGGACCTATTAGTAGGCGCGGCCACGATGTGCTCTGCG
HC-J6     ACGCAGGGCTTACGGACGCACATTGACATGGTTGTGATGTCCGCCACGCTCTGCTCCGCT
                *    * **       **  *  **        * **          **    *    ** ** **

JK1a      CTCTACGTGGGGGATCTGTGCGGGTCTGTCTTTCTTGTCGGCCAACTGTTTACCTTCTCT
```

FIG. 3B-1

```
JK2a     CTCTACGTGGGGGACCTCTGTGGCGGGATGATGCTCGCAGCCCAGATGTTCATCGTTTCG
JK2b     TTGTACGTAGGAGACGTGTGTGGGCTGTGATGATTGTGTCTCAGGCCCTTATAATATCA
SW83.2c  CTTTATGTGGGGGACGTGTGTGGCGCGCTGATGCTGGCCGCTCAGGTCGTCGTCGTGTCG
HTA23    CTTTACGTGGGGGACGTGTGTGGTGCGCTGATGATTGCCGCTCAGGTCGTCATTGTGTCT
HTA33    CTCTATGTGGGGGACGTGTGTGGCGCGTTGACGATAGCCGCTCAGGTTGTCATCGTATCG
HTA30    CTTTATGTGGGGGACGTGTGTGGCGCGTTGATGATAGCCGCCCAGGTCGTCATCGTATCG
HCV-1    CTCTACGTGGGGGACCTATGCGGGTCTGTCTTTCTTGTCGGCCAACTGTTCACCTTCTCT
HCV-J    ATGTACGTTGGGGATCTCTGCGGATCCGTTTTTCTCGTCTCCCAGCTGTTCACCTTCTCA
HC-J8    TTGTATGTGGGAGATGTGTGCGGGGCCGTGATGATTCTATCGCAGGCTTTCATGGTATCA
NZL-1    CTCTACGTGGGTGATATGTGTGGGGCTGTCTTTCTCGTGGGACAAGCCTTCACGTTCAGA
HC-J6    CTTTACGTGGGGGACCTCTGCGGTGGGGTGATGCTTGCAGCCCAGATGTTCATTGTCTCG
         *  **  ** ** **   * **  **        *       *     **     *       *

JK1a     CCCAGGCGCCACTGGACGACGCAAGGTTGCAAT
JK2a     CCGCAGAACCACTGGTTCGTGCAGGAATGCAAT
JK2b     CCAGAACACCATAACTTCACCCAAGAGTGCAAC
SW83.2c  CCACAACACCATACGTTTGTCCAGGAATGCAAC
HTA23    CCGCAGCATCACCACTTTGTCCAGGACTGCAAT
HTA33    CCACGGCACCACCACTTTGTCCAGGACTGCAAT
HTA30    CCACAGCACCACCACTTTGTCCACGACTGCAAC
HCV-1    CCCAGGCGCCACTGGACGACGCAAGGTTGCAAT
HCV-J    CCTCGCCGGTATGAGACGGTACAAGATTGCAAT
HC-J8    CCACAACGCCACAACTTCACCCAAGAGTGCAAC
NZL-1    CCTCGACGCCATCAAACGGTCCAGACCTGTAAC
HC-J6    CCACAGCACCACTGGTTTGTGCAAGACTGCAAT
         **       *        **      **  **
```

FIG. 3B-2

```
HTA3    TCATCCAACATCTAGTCTAGAGTGGCGGAATACGTCTGGCCTCTATGTCCTTACCAACGA
HTA7    TCATCCAACATCTAGTCTAGAGTGGCGGAATACGTCTGGCCTCTATGTCCTTACCAACGA
HTA18   TCATCCAACATCTAGTCTAGAGTGGCGGAATACGTCTGGCCTCTATGTCCTTACCAACGA
HTA20   TCATCCAACATCTAGTCTAGAGTGGCGGAATACGTCTGGCCTCTATGTCCTTACCAACGA
HTA22   TCATCCAACATCTAGTCTAGAGTGGCGGAATACGTCTGGCCTCTATGTCCTTACCAACGA
HTA26   TCATCCAACATCTAGTCTAGAGTGGCGGAATACGTCTGGCCTCTATGTCCTTACCAACGA
HTA35   TCATCCAACATCTAGTCTAGAGTGGCGGAATACGTCTGGCCTCTATGTCCTCACCAACGA
NZL-1   TCATCCAGCAGCCAGTCTAGAGTGGCGGAATACGTCTGGCCTCTACGTCCTTACCAACGA
HCV-1   TGTGCCCGCTTCGGCCTACCAAGTGCGCAACTCCACGGGGCTTTACCACGTCACCAATGA
HCV-J   CATCCCAGCTTCCGCTTACGAGGTGCGCAACGTGTCCGGGATATACCATGTCACGAACGA
HC-J6   CACCCCGGTCTCCGCTGCCGAAGTGAAGAACATCAGTACCGGCTACATGGTGACCAACGA
HC-J8   AGTGCCAGTGTCTGCAGTGGAAGTCAGGAACATTAGTTCTAGCTACTACGCCACTAATGA
             **   *   *    **       **     ** ** ** **

HTA3    CTGTTCCAATAACATTATTGTGTATGAGGCCGATGACGTCATCCTGCACACGCCCGGCTG
HTA7    CTGTTCCAATAACATCATTGTGTATGAGGCCGATGACGTCATCCTGCACGCACCCGGCTG
HTA18   CTGTTCCAATAATATTATTGTGTATGAGGCCGACGACGTCATCCTGCACGCCCCCGGCTG
HTA20   CTGTTCCAATAACATTATTGTGTATGAGGCCGATGACGTCATCCTGCACACACCCGGCTG
HTA22   CTGTTCCAATAACAGTATTGTGTATGAGGCCGATCACGTCATCCTGCACACACCCGGCTG
HTA26   CTGTTCTAATAACATTATTGTGTATGAGGCCGATGACGTCATCCTGCACACACCCGGCTG
HTA35   CTGTTCCAACAACATTATTGTGTATGAGGCCGATGACGTCATTCTGCACACGCCCGGCTG
NZL-1   CTGTTCCAATAGCAGTATTGTGTATGAGGCCGATGATGTCATTCTGCACACACCCGGCTG
HCV-1   TTGCCCTAACTCGAGTATTGTGTACGAGGCGGCCGATGCCATCCTGCACACTCCGGGGTG
HCV-J   CTGCTCCAACTCAAGTATTGTGTATGAGGCAGCGGACATGATCATGCACACCCCCGGGTG
HC-J6   CTGCACCAATGATAGCATTACCTGGCAACTCCAGGCTGCTGTCCTCCACGTCCCCGGGTG
HC-J8   TTGCTCAAACAACAGCATCACCTGGCAGCTCACTGACGCAGTTCTCCATCTTCCTGGATG
             ** * **    *  **        *   *           *   * **  ** ** **

HTA3    TGTACCTTGTGTTCAGGACGGTAATACATCCAAGTGCTGGACCCCAGTGACACCTACAGT
HTA7    TGTACCTTGTGTTCAGGACGGCAATACATCCACGTGCTGGACCCCAGTGACACCTACAGT
HTA18   TGTACCTTGTGTTCAGGACGGCAATACATCCACGTGCTGGATCCCAGTGACACCTACAGT
HTA20   TGTACCTTGTGTTCAGGACGGCAATACATCCACGTGCTGGACCCCAGTGACACCTACAGT
HTA22   TGTACCTTGTGTTCAAGCCAACAATAAATCCAAATGCTGGACCCCAGTGACACCTACAGT
HTA26   TGTACCTTGTGTTCAGGACGGCAATGCATCCACGTGCTGGACCCCAGTAACACCTACAGT
HTA35   CGTACCTTGTGTACAGGACGGCAATACATCCACGTGCTGGACCCCAGTGACACCTACAGT
NZL-1   TGTACCTTGTGTCCAGGACGGCAATACATCTACGTGCTGGACCCCAGTGACACCTACAGT
HCV-1   CGTCCCTTGCGTTCGTGAGGGCAACGCCTCGAGGTGTTGGGTGGCGATGACCCCTACGGT
HCV-J   CGTGCCCTGCGTCCGGGAGAGTAATTTCTCCCGTTGCTGGGTAGCGCTCACTCCCACGCT
HC-J6   CGTCCCGTGCGAGAAAGTGGGGAATACATCTCGGTGCTGGATACCGGTCTCACCGAATGT
HC-J8   CGTCCCATGTGAGAATGATAATGGCACCTTGCATTGCTGGATACAAGTAACACCCAACGT
         ** ** ** *    *       *         ** ***     *  ** *    *

HTA3    GGCAGTCAGGTACGTCGGAGCAACCACCGCTTCAATACGCAGCCACGTGGACCTATTATT
HTA7    GGCAGTCAGGTACGTCGGAGCAACCAGCGCTTCAATACGCAGCCATGTGGACCTATTAGT
HTA18   GGCAGTCAGGTACGCCGGAGCAACCACCGCTTCAATACGCAGCCATGTGGACCTGTTAGT
HTA20   ATCAGTCAGGTACGTCGGAGCAACCACCGCTTCAATACGCAGCCATGTGGACCTACTATT
HTA22   ATCAGTCGAGTACGTCGGAGCAACCACCGCTTCAATACGCAGCCATGTGGACCTACTATT
HTA26   ATCAGTCAGGTACGTCGGAGCAACCACCGCTTCAGTACGCAGCCATGTGGACCTACTATT
HTA35   GGCAGTCAGGTACGTCGGAGCAACTACCGCTTCAATACGCAGCCATGTGGACCTATTATT
NZL-1   GGCAGTCAGGTACGTCGGAGCAACTACTGCTTCGATACGCAGTCATGTGGACCTATTAGT
HCV-1   GGCCACCAGGGATGGCAAACTCCCCGCGACGCAGCTTCGACGTCACATCGATCTGCTTGT
HCV-J   CGCGGCCAGGAACAGCAGCATCCCCACCACGACAATACGACGCCACGTCGATTTGCTCGT
HC-J6   GGCCGTGCAGCAGCCCGGCGCCCTCACGCAGGGCTTACGGACGCACATTGACATGGTTGT
HC-J8   GGCTGTGAAACACCGCGGTGCGCTCACTCGTAGCCTGCGAACACACGTCGACATGATCGT
         *       *       *       *  **    ** *  **     *  *   *

HTA3    GGGCGCGGCCACGATGTGCTCTGCGCTCTACGTGGGT
```

FIG. 3C-1

| | |
|---|---|
| HTA7   | GGGCGCGGCCACGATGTGCTCTGCGCTCTACGTGGGT |
| HTA18  | GGGCGCGGCCACGATGTGCTCTGCGCTCTACGTGGGT |
| HTA20  | GGGCGCGGCCACGATGTGCTCCGCGCTCTACGTGGGT |
| HTA22  | GGGCGCGGCCACGATGTGCTCTGCGCTCTACGTGGGT |
| HTA26  | GGGCGCGGCCACGATGTGCTCTGCGCTCTATGTGGGT |
| HTA35  | GGGCGCGGCCACGATGTGCTCTGCGCTCTACGTGGGT |
| NZL-1  | AGGCGCGGCCACGATGTGCTCTGCGCTCTACGTGGGT |
| HCV-1  | CGGGAGCGCCACCCTCTGTTCGGCCCTCTACGTGGGG |
| HCV-J  | TGGGGCGGCTGCTCTCTGTTCCGCTATGTACGTTGGG |
| HC-J6  | GATGTCCGCCACGCTCTGCTCCGCTCTTTACGTGGGG |
| HC-J8  | AATGGCAGCTACGGCCTGCTCGGCCTTGTATGTGGGA |
| | **  *   ** ** **  * ** ** ** |

FIG. 3C-2

```
HC-J6    -GCAGAAAGCGTCTAGCCATGGCGTTAGTATGAGTGTCGTACAGCCTCCAGGCCCCCCC
HC-J8    -GCAGAAAGCGTCTAGCCATGGCGTTAGTATGAGTGTCGTACAGCCTCCAGGCCCCCCC
HC-J4    -GCAGAAAGCGTCTAGCCATGGCGTTAGTATGAGTGTCGTGCAGCCTCCAGGACCCCCC
HCV-1    -GCAGAAAGCGTCTAGCCATGGCGTTAGTATGAGTGTCGTGCAGCCTCCAGGACCCCCC
NZL1     -GCGGAAAGCGCCTAGCCATGGCGTTAGTACGAGTGTCGTGCAGCCTCCAGGACCCCCC
S83      -GCAGAAAGCGTCTAGCCATGGCGTTAGTATGAGTGTCGTACAGCCTCCAGGCCCCCCC
HTA23    -GCAGAAAGCGTCTAGCCATGGCGTTAGTATGAGTGTCGTACAGCCTCCAGGCCCCCCC
HTA30    -GCAGAAAGCGTCTAGCCATGGCGTTAGTATGAGTGTCGTACAGCCTCCAGGCCCCCCC
HTA33    GGCAGAAAGCGTCTAGCCATGGCGTTAGTATGAGTGTCGTACAGCCTCCAGGTCCCCCC
          **  ******  ****************** ********  *********** ******

HC-J6    TCCCGGGAGAGCCATAGTGGTCTGCGGAACCGGTGAGTACACCGGAATTGCCGGGAAGAC
HC-J8    TCCCGGGAGAGCCATAGTGGTCTGCGGAACCGGTGAGTACACCGGAATTACCGGAAAGAC
HC-J4    TCCCGGGAGAGCCATAGTGGTCTGCGGAACCGGTGAGTACACCGGAATTGCCAGGACGAC
HCV-1    TCCCGGGAGAGCCATAGTGGTCTGCGGAACCGGTGAGTACACCGGAATTGCCAGGACGAC
NZL1     TCCCGGGAGAGCCATAGTGGTCTGCGGAACCGGTGAGTACACCGGAATCGCTGGGGTGAC
S83      TCCCGGGAGAGCCATAGTGGTCTGCGGAACCGGTGAGTACACCGGAATTGCCGGGAAGAC
HTA23    TCCCGGGAGAGCCATAGTGGTCTGCGGAACCGGTGAGTACACCGGAATTGCCGGGAAGAC
HTA30    TCCCGGGAGAGCCATAGTGGTCTGCGGAACCGGTGAGTACACCGGAATTGCCAGGAAGAC
HTA33    TCCCGGGAGAGCCATAGTGGTCTGCGGAACCGGTGAGTACACCGGAATTGCCGGGAAGAC
          **********************************************  *  *  ***

HC-J6    TGGGTCCTTTCTTGGATAAACCCACTCTATGCCCGGTCATTTGGGCGTGCCCCCGCAAGA
HC-J8    TGGGTCCTTTCTTGGATAAACCCACTCTATGTCCGGTCATTTGGGCACGCCCCCGCAAGA
HC-J4    CGGGTCCTTTCTTGGATCAACCCGCTCAATGCCTGGAGATTTGGGCGTGCCCCCGCGAGA
HCV-1    CGGGTCCTTTCTTGGATCAACCCGCTCAATGCCTGGAGATTTGGGCGTGCCCCCGCAAGA
NZL1     CGGGTCCTTTCTTGGAGCAACCCGCTCAATACCCAGAAATTTGGGCGTGCCCCCGCGAGA
S83      TGGGTCCTTTCTTGGATAAACCCACTCTATGCCCGGCCATTTGGGCGTGCCCCCGCAAGA
HTA23    TGGGTCCTTTCTTGGATAAACCCACTCTATGCCCGGCCATTTGGGCGTGCCCCCGCAAGA
HTA30    TGGGTCCTTTCTTGGATAAACCCACTCTATGCCTGGCCATTTGGGCGTGCCCCCGCAAGA
HTA33    TGGGTCCTTTCTTGGATAAACCCACTCTATGCCCGGCCATTTGGGCGTGCCCCCGCAAGA
          **************  ***** ***  *  *  *  ******* ******* ***

HC-J6    CTGCTAGCCGAGTAC
HC-J8    CTGCTAGCCGAGTAC
HC-J4    CTGCTAGCCGAGTAC
HCV-1    CTGCTAGCCGAGTAC
NZL1     TCACTAGCCGAGTAC
S83      CTGCTAGCCGAGTAC
HTA23    CTGCTAGCCGAGTAC
HTA30    CTGCTAGCCGAGTAC
HTA33    CTGCTAGCCGAGTAG
           ***********
```

FIG. 3D

HETERODUPLEX TRACKING ASSAY (HTA) FOR GENOTYPING HCV

FIELD OF THE INVENTION

This invention relates to genotyping hepatitis C viruses (HCV). In particular, this invention relates to specific primers preferably from the core and envelope region of HCV and a method to determine genotypes of HCV with a heteroduplex mobility or tracking assay which in turn utilizes specific primers.

BACKGROUND OF THE INVENTION

Viral hepatitis is known to be caused by five different viruses known as hepatitis A, B, C, D, and E. HAV is an RNA virus and does not lead to long-term clinical symptoms. HBV is a DNA virus. HDV is a dependent virus that is unable to infect cells in the absence of HBV. HEV is a water-borne virus. HCV was first identified and characterized as a cause of non-A, non-B hepatitis NANBH. (Houghton et al., EPO Pub. Nos. 388,232 and 318,216). This led to the disclosure of a number of general and specific polypeptides useful as immunological reagents in identifying HCV. See, e.g., Choo et al. (1989) *Science,* 244:359–262; Kuo et al., (1989) *Science* 244:362–364 and Houghton et al, (1991) *Hepatology* 14:381–388.

HCV is a single stranded RNA virus, distantly related to the pestivirus and flavivirus and it is the causative agent of the vast majority of transfusion-associated hepatitis and of most cases of community-acquired non-A, non-B hepatitis worldwide. The HCV genome consists of 5' and 3' noncoding (NC) regions that flank a single long open reading frame (ORF). This ORF encodes for three structural proteins at the amino-terminal end and for six nonstructural (NS) proteins at the carboxyl-terminal end. The structural proteins are represented from the nucleocapsid (core; C) proteins and two glycoproteins, envelope 1 (E1) and envelope 2 (E2). The nonstructural proteins are named NS2, P7, NS3, NS4a, NS4b, NS5a, NS5b. The 5'NCR is the most highly conserved part of the HCV genome, whereas the sequence of the two envelope proteins (E1 and E2) is highly variable among different HCV isolates. The highest degree of variation has been observed in a region within E2, now commonly termed hypervariable region 1 (HVR1) or E2HV. A second variable region called the HVR2 also exists in a subset of isolates. Typically, the genetic heterogeneity of HCV has been classified under two headings: quasispecies and genotype. As used herein the term "quasispecies" refers to the genetic heterogeneity of the HCV population within an infected individual. As used herein the terms "genotype" and "subtype" refer to the genomic heterogeneity observed among different HCV isolates. The analysis of nucleic acid sequence variation of the HCV genome, a positive stranded RNA molecule of approximately 9.4 kb, suggest that genetic variability is associated with important virological and clinical implications.

The prototype isolate of HCV was characterized in EP Publications Nos. 318,216 and 388,232. As used herein, the term "HCV" includes newly isolated NANBH viral species. The term "HCV-1" refers to the virus described in the above-mentioned publications.

Since the initial identification of HCV, at least 6 different major viral types have been identified (full length genomes reported) and designated Type 1, 2, 3, 4, 5 and 6. Within these types are numerous subtypes. The type of virus with which a patient is infected may affect the clinical prognosis and also response to various treatments. See, Yoshioke et al., (1992) *Hepatology* 16:293–299. Considering that the most serious clinical outcome of HCV infection is heptocellular carcinoma, it would be useful to be able to determine with which type or types of HCV a patient is infected. It is thus of particular importance to develop an, accurate, reliable assay for HCV genotyping and subtyping, that, without requiring the sequencing, could also give the genetic divergence intra-subtype. Several classification have been proposed for HCV genotyping based on analysis of different regions, because the ideal nucleotide sequence-based system, using the complete viral genome is not practical.

SUMMARY OF THE INVENTION

The present invention includes primers and methods for the characterization of HCV genotyping and of variation intra-subtype based on the heteroduplex tracking assay (HTA). The preferred probes/primers were single stranded derived from the carboxyl terminus of core and part of the E1 region of HCV.

The HTA is a hybridization based method of determining the genetic relationship between two or more viral genomes. The basis of the method is that related DNA products co-amplified from divergent templates reanneal randomly to form heteroduplexes that migrate with reduced mobility in systems designed to separate molecules on the basis of size such as neutral polyacrylamide gels, HTA was originally used to genotype HIV-1 and to follow the in vivo evolution of HIV-1 in patients and populations. See, e.g., Delwart et al., (1993) *Science* 262:1757–1261 and Delwart et al., (1994) *J. Virol.* 68:6772–6883.

One aspect of the invention is a method for genotyping HCV comprising the steps of denaturing and reannealing partially complementary DNA or RNA strands and detecting sequence variation by noting electrophoretic mobility of the DNA heteroduplexes on a system designed to separate moleculte on the basis of size such as by following electrophoresis through a polyacrylamide or MDE gel.

Another aspect of the invention relates to the probes used in the genotyping which were selected from the core and E1 region of the HCV genome.

Another aspect of the invention relates to a method of predicting the response to drug therapy of a patient infected with a strain of HCV by determining the sensitivity of different known genotypes to drug therapy, determining the genotype of the HCV strain infecting the patient and comparing the genotype with its sensitivity to predict the patient's response to the drug therapy.

Another aspect of the invention relates to therapeutic vaccines and predicting which therapeutic vaccine should be utilized by determining the genotype of a strain of HCV in an HCV-infected patient and administering a therapeutic vaccine of the same genotype.

Another aspect of the invention relates to prophylatic vaccines and predicting which vaccine should be administered to a certain population sample by determining the prevalent genotypes in a like sample and administering a prophylatic vaccine of a genotype likely to be the prevalent genotype to the population sample.

Another aspect of the invention relates to the ability to discover new genotypes of HCV using the method of the invention.

BRIEF DESCRIPTION OF THE FIGURES

FIGS. 3A–3D show the nucleotide sequences for dendograms depicted in FIGS. 2A–2D.

DESCRIPTION OF THE INVENTION

Figure 1A:
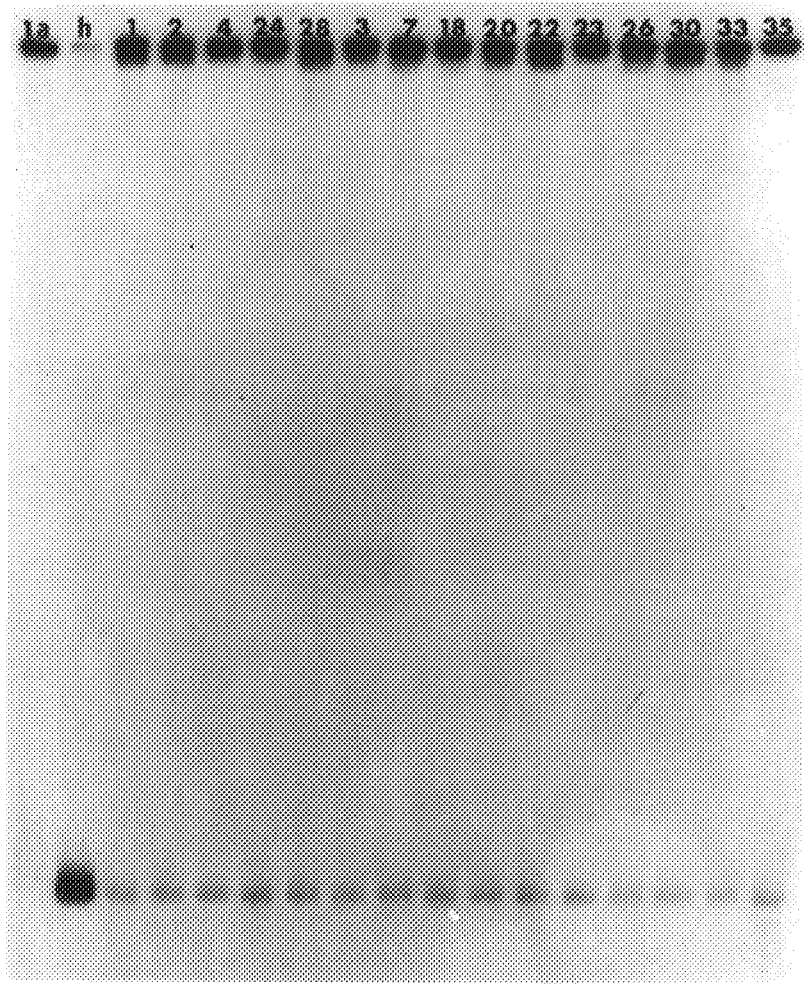
FIGS. 1A–1E are autoradiograms showing homoduplexes and heteroduplexes of the samples to be typed with the probes of known genotypes (ss probes are of genotypes 1a, 1b, 2a, 2b, 3a in FIGS. 1A–1E respectively, lane on far left of MDE gel). The homoduplex (h) (ss probe to the double stranded RT-PCR product of known genotype from which it was derived) is shown adjacent to the probe. The heteroduplexes of the RT-PCR products from the 15 dialysis patients (nos. 1, 2, 3, 4, 7, 18, 20, 22, 23, 24, 26, 28, 30, 33, 35) hybridized to the ss probe is designated above the appropriate lane in each Figure.

The practice of the present invention will employ, unless otherwise indicated, conventional techniques of molecular biology, microbiology, recombinant DNA, polypeptide and nucleic acid synthesis, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.),and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or(3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

By "PCR" is meant herein the polymerase chain reaction (PCR) technique, disclosed by Mullis in U.S. Pat. Nos. 4,683,195 (Mullis et al) and 4,683,202, incorporated herein by reference. In the PCR technique, short oligonucleotide primers are prepared which match opposite ends of a desired sequence. The sequence between the primers need not be known. A sample of DNA (or RNA) is extracted and denatured (preferably by heat). Then, oligonucleotide primers are added in molar excess, along with dNTPs and a polymerase (preferably Taq polymerase, which is stable to heat). The DNA is replicated, then again denatured. This results in two "long products," which begin with the respective primers, and the two original strands (per duplex DNA molecule). The reaction mixture is then returned to polymerizing conditions (e.g., by lowering the temperature, inactivating a denaturing agent, or adding more polymerase), and a second cycle initiated. The second cycle provides the two original strands, the two long products from cycle 1, two new long products (replicated from the original strands), and two "short products" replicated from the long products. The short products have the sequence of the target sequence (sense or antisense) with a primer at each end. On each additional cycle, an additional two long products are produced, and a number of short products equal to the number of long and short products remaining at the end of the previous cycle. Thus, the number of short products grows exponentially with each cycle. This amplification of a specific analyte sequence allows the detection of extremely small quantities of DNA.

The term "3 SR" as used herein refers to a method of target nucleic acid amplification also known as the "self-sustained sequence replication" system as described in European Patent Publication No. 373,960 (published Jun. 20, 1990).

The term "LCR" as used herein refers to a method of target nucleic acid amplification also known as the "ligase chain reaction" as described by Barany, Proc. Natl. Acad. Sci. (USA) (1991) 88:189–193.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via MRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

The protein may be used for producing antibodies, either monoclonal or polyclonal, specific to the protein. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

By "cDNA" is meant a complimentary mRNA sequence that hybridizes to a complimentary strand of mRNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

By "pharmaceutical acceptable carrier," is meant any pharmaceutical carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art. Preferably Calcitonin, a polypeptide hormone produced by C-cells.

The therapeutic compositions typically will contain pharmaceutically acceptable vehicles, such as water, saline, glycerol, ethanol, etc. Additionally, auxiliary substances, such as wetting or emulsifying agents, pH buffering substances, and the like, may be present in such vehicles.

Typically, the therapeutic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect.

Evidence indicates that different HCV geneotypes may have different pathogenicities as well as distinct geographical distributions and may elicit partly different serological profiles in infected patients. See Cammarota, et al. *J. Clin. Microb.* (1995) 33:2781–2784. The invention includes methods for detecting HCV and identifying infection by different types of HCV. The invention includes genotyping HCV, the potential to discover new genotypes, and assessing viral populations to predict response to drug therapy, prepare therapeutic vaccines as well as the choice of prophylatic vaccines. The invention also includes probes for use in the genotyping of HCV.

The methods for genotyping HCV include but are not limited to a heteroduplex tracking or mobility assay utilizing probes/primers from the core/E1 region of the HCV genome. The documented antigenic differences between HCV genotypes would have usefulness not donors only in blood donors screening and in predicting the response to IFN treatment but also for designating the composition of candidate vaccines for HCV in different countries, choice of therapeutic vaccines as well as in the identification of new genotypes. Other methods have been proposed to identify the main genotypes infecting populations, based on analysis of different regions of the genome, such as RFLP. See Davidson et al., J. Gen Virol. (1995) 76:1197–1204 for discussion of genotyping HCV using RFCP of sequences co-amplified form the 5' non-coding region (NCR).

The known nucleic acid based methods of genotyping require (1) sub-type specific RT-PCR(reverse transcriptase-PCR) primers (see Okamoto (1992) J. Gen Virol 73:673–679) U.S. Pat. No. 5,427,909; (2) specific probes (G. Marteen, et al., Line probe assay); (3) restriction site polymorphism (a function of the nucleotide sequence (nt)) or (4) direct sequences to determine genotype. The analysis of the 5' NC sequence with RFLP is easy to performed, but does not accurately predict all HCV genotypes, and, some subtypes may be misclassified. For example, the change in sequence between 1a and 1b recognized by the restriction enzyme is not absolute and sequences other than 1a and 1b, 2a and 2b are misclassified. For example, type 1c would appear as type 1a, type 2c as either type 2a or 2b. See Cammarota et al., *J. Clin. Microb.*, (1995) 33:2781–2784. For this reason, RFLP is not able to detect "escape" species, new divergent species, or epidemiological trends. It is likely that a typing method like RFLP will have to be continuously modified to accommodate the rapidly increasing amount of information collected on HCV sequence heterogeneity.

As mentioned above, when using the nucleic acid based methods of genotyping, one obtains a result of either a type or subtype or a negative that is "untypeable" result. See, e.g. Cammarota, et al., J. Clin. Microb. (1995) 33:2781–2784, isolates that remained untyped by genotype-specific PCR were classified subtype 2C on the basis of sequence analysis of PCR amplifications obtained from the core and NS5 genes. This problem is avoided by using the presently claimed invention to determine HCV genotypes by choosing RT-PCR primers in the C-terminus or core/mid ⅔ of E1. In addition, the subtype of the isolate can be accurately determined using the present invention of HCV genotyping and isolates can be detected, even those less than in approximately 30% divergent, enabling the characterization of new sub-types without sequencing.

Heteroduplex Tracking or Mobility Assay

The method of determining the genotype of HCV in the present invention utilizes minor variants in complex quasispecies. One such technique is the heteroduplex tracking assay (HTA). HTA, well known in which the art for use with HIV, (see e.g., Delwart,et al., J. Virol. (1994) 68:6672–6683; Delwart, et al., Science (1993) 262:1257–1261; Delwart, et al., PCR Methods and Applications 4:S202–S216 (19950 Cold Springs Harbor; and Delwart, et al., Heteroduplex Mobility Analysis HIV-1 env Subtyping Kit Protocol Version 3, each of which is incorporated herein by reference in its entirety), grew out of the observation that when sequences were amplified by nested PCR from peripheral blood mononuclear cells of infected individuals, related DNA products coamplified from divergent templates could randomly reanneal to form heteroduplexes that migrate with reduced mobility in neutral polyacrylamide gels. Using these techniques, one can establish genetic relationships between multiple viral DNA template molecules.

HTA in particular utilizes a first PCR product as a labeled probe, it may be radioactive, which is mixed with an excess (driver) of an unlabeled PCR product from a different source, i.e., the source for which typing is desired. The probe sequences are then driven completely into heteroduplexes with the driver, and are separated on the basis of size. An autoradiogram for example of the resulting polyacrylamide gel reveals only these heteroduplexes and provides a visual display of the relationship between the two virus populations under study. The fact that heteroduplexes migrate with distinct mobilities indicates that the strand-specific composition of mismatched and unpaired nucleotides affects their mobility.

An exponential equation described in Delwart et al., is then used to describe a curve fitting the experimental data from pairwise analysis of genes of known sequence. In the present invention, the equation is used to estimate the genetic distance between the known genotypes of the probes and the unknown genotypes of the patient samples.

Primers for Use in the HTA

It was determined that the E1 or core region could be the best region in which to study HCV heterogeneity, thus the E1 region became the choice for primers in the present invention. The use of the partial E1 sequence, the most heterogeneous region of the genome for the present invention, as well as a longer fragment, i.e. 400 nt, althought it could have been as long as 1000 nt, enabled the design of probes which do not cross-hybridize among sub-types/types and thus allow accurate genotyping. By flanking the heterogeneous region, conserved nt sequences for sense and anti-sense primers were identified. Preferably, a combination of universal sense and type specific antisense primers for the first PCR round and a universal antisense and type specific sense primers for the second round were utilized. The PCR need not be two rounds and the primers are not limited to the above-described combination. However, the preferred combination enabled the preparation of single stranded probes and minimized the number of PCR primer combinations.

Preferred probes are sequences in the core and E1 region. The sequences of these regions for a wide range of genotypes are published and grouped into at least 12 distinct genotypes and subtype: I/1a, II/1b, III/2a, IV/2b, 2c, 3a, 4a, 4b, 4c, 4d,5a, 6a. The nucleotide sequence identity of the E1 gene among HCV isolates of the same genotype ranges from 88.0% to 99.1%, whereas the identity of HCV isolates of different genotypes ranges from 53.5 to 78.6%. The degree of variation for good discrimination of heteroduplex in neutral polyacrylamide gels is comfortably within the range of 3–20%, so that is likely that divergent templates reanneal to form a heteroduplex if they are of the same subtype. For this reason a single stranded 32p labelled DNA probe was used so that if the formation of the heteroduplex is impossible, the ss-DNA probe could likely not reanneal and form a homoduplex band. Without direct sequencing, the present invention can rapidly give not only a certain identification of the subtypes, but also the genetic relations inside the same. For example, the genotypes analyzed, i.e., (1a, 1b, 2a, 2b, 3a) showed no overlap between different subtypes.

Further since isolates approximately 30% divergent can be visualized on the gel, new subtypes can be visualized and the distribution of isolates in a population could be characterized and populations or individual isolates can be followed in a population or in individuals in epidemiological studies.

HCV Genotyping Kits

A kit for determining the genotype of HCV is within the scope of this invention. As described for HIV in Delwart et al, Heteroduplex Mobility Analysis HIV-1 env Subtyping Kit Protocol Version 3, such a kit would include the specific primers. Preferred primers are from the core and E1 region of the HCV genome. If two stages of PCR are desired, the first round primers could include for example a universal sense probe, preferably located in the core/E1 region of the HCV genome. One such universal primer is located from nucleotide 508 to 529 (SEQ ID NO: 1) of HCV-1 and is shown in Table 1. Coupled with the universal primer could be a type specific antisense primer also preferably located in the core/E1 region of the HCV genome. Examples of these primers are from nucleotides 1032 to 1012 for type 1 (SEQ ID NO: 2), type 2a (SEQ ID NO: 3), type 2b (SEQ ID NO:4) and type 3a (SEQ ID NO: 5) of the HCV genomes and are also shown in Table 1.

If a second round of PCR is desired, the second round primers would likewise be from the core/E1 region of the HCV genome. Preferred second round primers could include a universal antisense primer from nucleotides 978 to 958 (SEQ ID NO: 6) of the HCV-1 genome, this primer is shown in Table 1. In addition the second round primers could include a type specific sense primer from the core/E1 region. Preferred second round type specific sense primers are from nucleotides 536 to 557 of HCV genomes type 1 (SEQ ID NO: 7), type 2 (SEQ ID NO: 8) or type 3 (SEQ ID NO: 9), and are shown in Table 1.

The first or second round of primers may be sufficient to amplify the viral RNA without using a second round of PCR if the concentration of the virus is sufficiently high, ie., nested PCR is not necessarily required, what is required is PCR products in 100× excess of probe.

An HCV genotyping kit of the present invention would also include subtype references which may change as new subtypes are discovered and evaluated for use in the kit. Use of more than one reference from a given subtype is recommended because comparison to a single reference does not always provide an unambiguous result.

The foregoing discussion and following examples only illustrate the invention, persons of ordinary skill in the art will appreciate that the invention can be implemented in other ways, and the invention is defined solely by reference to the claims.

EXAMPLE 1

Patient Samples 35 hemodialyzed patients undergoing regular hemodialysis were studied: 20 men (57%) and 15 women (43%) with a mean age of 64.8±13 years. Serum samples were collected in August 1995, divided into aliquots and stored at −80 degrees Celsius. 26 patients were anti-HCV ELISA positive and 9 anti-HCV ELISA negative. 25 of the 26 ELISA positive were also RIBA III positive, while 1 was indeterminate. The 9 ELISA negative were all RIBA III negative. 15 patients were HCV-RNA 5' UTR and E1 PCR positive. By direct sequencing of 15 5' NCR products, 5 patients resulted type 1; 3 patients type 2; and 7 patients type 3.

ers. A second RNA extraction was performed for RFLP and/or HTA to confirm the results. The primers used for the HTA are listed in Table 1. The nested pairs of PCR primers used to obtain these E1 products were different for the types 1, 2a, 2b, and 3a. The universal sense probe for the first round of amplification corresponds to 5'-3' nt 508–529, amino acids 170–176, of Choo, et al., PNAs, 1991, while the universal antisense primer for the second round of amplification corresponds to nt 978–958, amino acids 320–326 of Choo, et al., PNAS, 1991.

When the SS DNA DNA probes were prepared for use in the HTA, one of the primers for the nested PCR was biotinylated. See e.g. SEQ ID NO:6 in Table 1.

TABLE 1

| HCV | 5'→3' nt | 3'→5' nt | ~aa | | PCR |
|---|---|---|---|---|---|
| 1   SEQ ID NO:1 CCTGGTTGCTCTTTCTCTATCT #, purified, C170S | 508–529 | | ~170–176 | universal sense probe | I |
| 1   SEQ ID NO:2 GATGGCTTGTGGGATCCGGAG #, purified, E338A1 | 1032–1012 | 1012–1032 | 338–344 | Type 1 antisense | I |
| 1   SEQ ID NO:3 GATGACCTCGGGGACGCGCAT #, purified, E338A2a | 1032–1012 | 1012–1032 | " | Type 2a antisense | I |
| 1   SEQ ID NO:4 GACCAGTTCTGGAACACGAGC #, purified, E338A2b | 1032–1012 | 1012–1032 | " | Type 2b antisense | I |
| 1   SEQ ID NO:5 CAAGGTCTGGGGTAAACGCAG #, purified, E338A3a | 1032–1012 | 1012–1032 | " | Type 3a antisense | II |
| 1   SEQ ID NO:6 CCAGTTCATCATCATATCCCA #, purified, E320A | 978–958 | 958–978 | ~320–326 | universal antisense | II |
| 1   SEQ ID NO:7 TGGCCCTGCTCTCTTGCTTGAC #, purified, C179S1 | 536–557 | " | ~179–186 | Type 1 sense | II |
| 1   SEQ ID NO:8 TTGCTCTTCTGTCGTGCGTCAC #, purified, C179S2 | 536–557 | " | " | Type 2 sense | II |
| 1   SEQ ID NO:9 TTGCTCTGTTCTCTTGCTTAAT #, purified, C179S3 | 536–557 | " | " | Type 3 sense | II |

EXAMPLE 2 cDNA and PCR

HCV-RNA was extracted at least two different times in a method using Stratagene reagent from a Strategene RNA Isolation Kit (Chomezynsky and Sacchi method).

RNA extracted from 20 ul of plasma was reverse transcribed in a 25 ul aliquot of cDNA mixture (BRL cDNA synthesis kit, 8085SB) using 100 pmol of PCR primers. The cDNA mixture was boiled for 5 minutes, quick-cooled on ice and added to the PCR cDNA reagents with final concentrations according to the Perkin PCR kit (N801-0055) specification. 40 PCR cycles (94 degrees Celsius for 10 seconds, 55 degrees Celsius for 30 seconds and 72 degrees Celsius for 30 seconds were performed. Ten ul of the first PCR reaction mixture was added to a second PCR reaction mixture containing nested PCR primers and was amplified for 40 cycles as indicated above.

The first extraction was used for the nested-PCR reaction with primers specific for the 5' NCR as previously described in Shimizu et al, PNAS (1992) 5477–5481 and this product was directly sequenced and used for the RFLP. RNA from the same extraction was used for HTA using core/E1 prim-

EXAMPLE 3

HTA

The single stranded probes were prepared by RT-PCR of HCV ELISA and RIBA positive era of known genotypes with the same PCR primers described above, except that one of the primers 320A was biotinylated. ssDNA probes were generated with the Dynabeads M-280 Streptavidin following the protocol of Heng Pan and Eric Delwart. The non-biotinylated single strand was eluted was from the magnetic bead/streptavidin column. Probes were generated from 20 ng of ss DNA of the different genotypes and end labeled using T4 polynucleotide kinase (Gibco BRL) and 100 microCi of 32P ATP and then column purified. The kinase probe was separated from 32 PATP using a Pharmaccia Bio Sepharose column. The 32P-labeled single strand probes were mixed with a 100-fold excess driver, PCR products were generated from the patient samples or the control serum/plasma. Hybridization was in 2×SSC. The mixtures were put on a 94 degree Celsius heat block for 3 minutes. They were then transferred to a 55 degree Celsius heat block for at least 2 hours. The entire reaction volume was loaded on 1 mm thick, 6% polyacrylamide MDE gel (Baker) and electrophoresed for 16 h at 500 V. The gel was vacuum dried at 80 degrees Celsius on filter paper and exposed to X-ray film. The genotypes of each of the samples were determined based on the Delwart method. Table 2 depicts the genotype results determined by using HTA.

FIGS. 1A–1E are antoradiograms showing each of the single strand probes in Table 1, that is the probes specific for known genotypes 1a, 1b, 2a, 2b, 3a in FIGS. 1A–1E respectively, see the lane on the far left of the MDE gel. The homoduplex(h) (ss probe to the double stranded RT-PCR product from which it was derived) is shown adjacent to the probe. RT-PCR products from the 15 dialysis patients (nos. 1, 2, 3, 4, 7, 18, 20, 22, 23, 24, 26, 28, 30, 33, 35) hybridized to the probe is designated also as the appropriate lane in each Figure.

As can be seen in FIGS. 1A–1E, Type 1 ss subtypes probes were specific for each type 1 sub-type and did not cross-hybridize with other subtypes 1b, 2a, 2b, 3a (2a, 2b not shown). Type 3a ss sub-type specific probe was also specific for subtype 3a and did not cross-hybridized with 1a, 2c, or 2a, 2s isolates (data not shown). SS Sub-type 2 probes do not cross-hybridize with each other (data not shown) but did cross-hybridize with subtype 2c isolates; however, the distance between the homoduplex and the 2c isolates indicates a high degree of divergence suggesting that patients 23, 30 and 33 had different sub-types. The virus in sera 23, 30 and 33 was confirmed by sequencing the partial E1 and found to be most closely related to sub-type 2c (see FIG. 2b) but was ambiguous by 51UTR sequencing, See FIG. 2D.

Figure 1B:
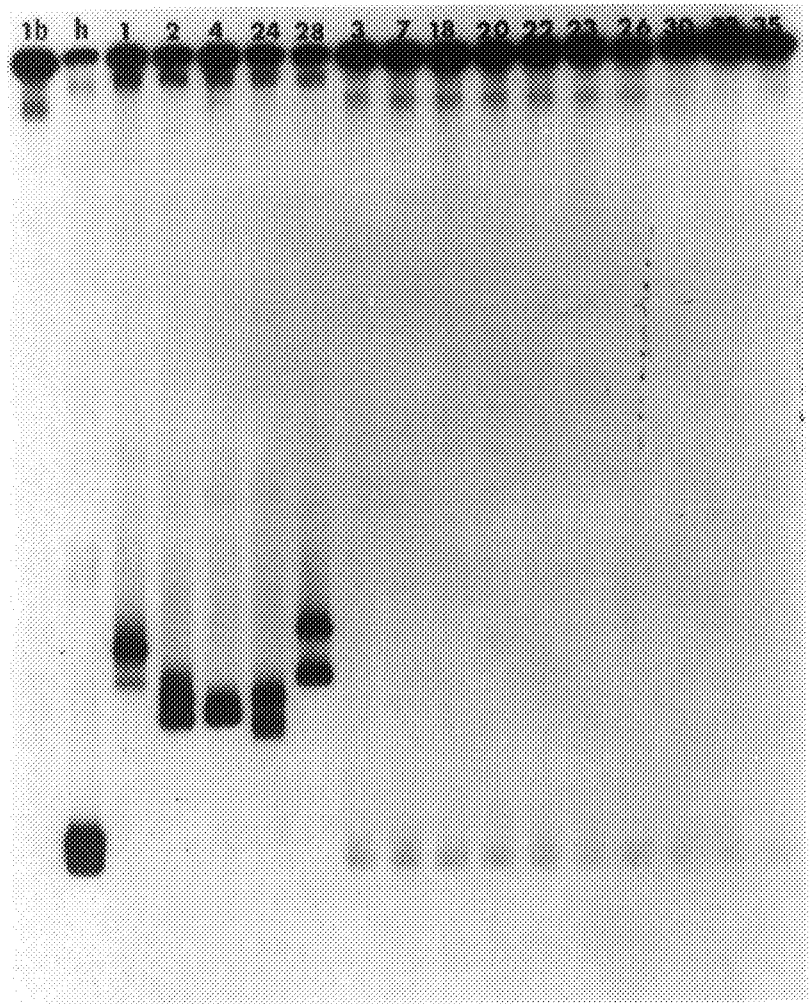
Figure 1C:
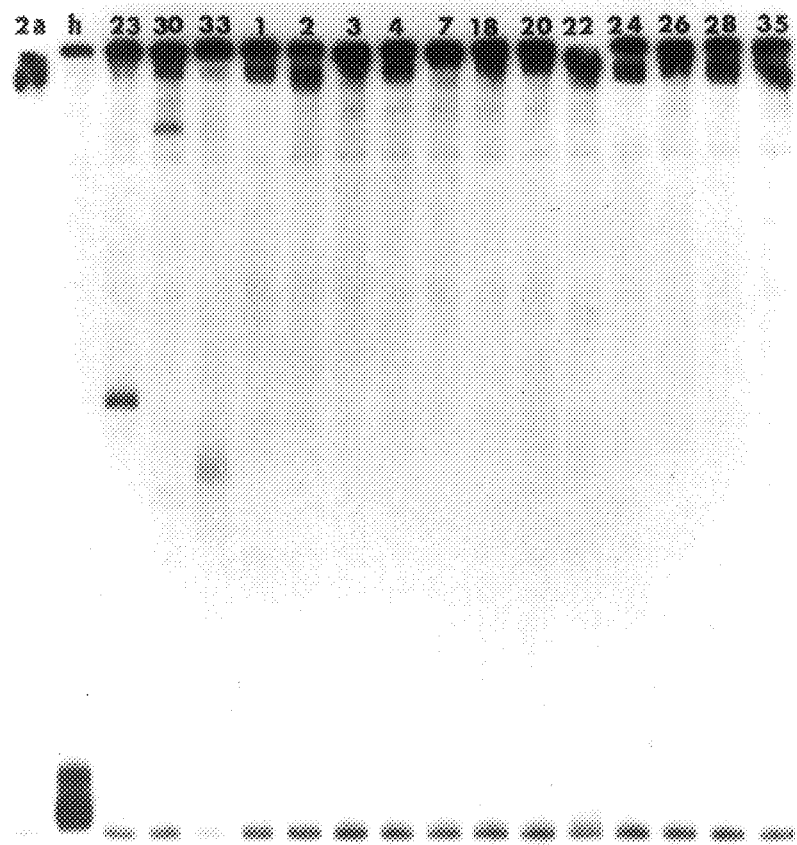
Figure 1D:
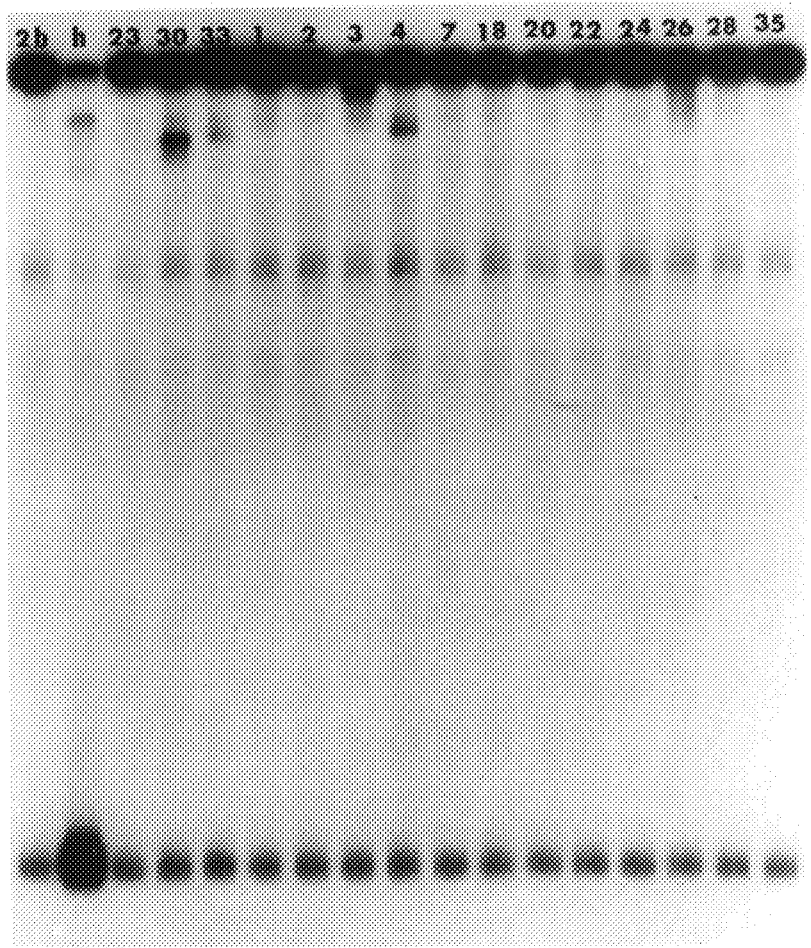

Isolates 23, 30 and 33 hybridized with the 2a probe, while only 30 and 33 hybridized to the 2b probe. The gels also indicate that isolate 30 is more closely related to 2a than to 2b. Therefore, while all three sera are clearly type 2 non-a, non-b subtype, they are not all equally divergent from types 2a and 2b. As seen in FIGS. 1B and 1D, patient 4 appears to be co-infected with types 1b and a non-a, non-b type subtype.

The 1b probe was derived from a patient (JK 16) and appeared to have two viral genomes which is reflected in the homoduplex lane (h) and therefore each 1b patient has two bands.

Figure 1E:
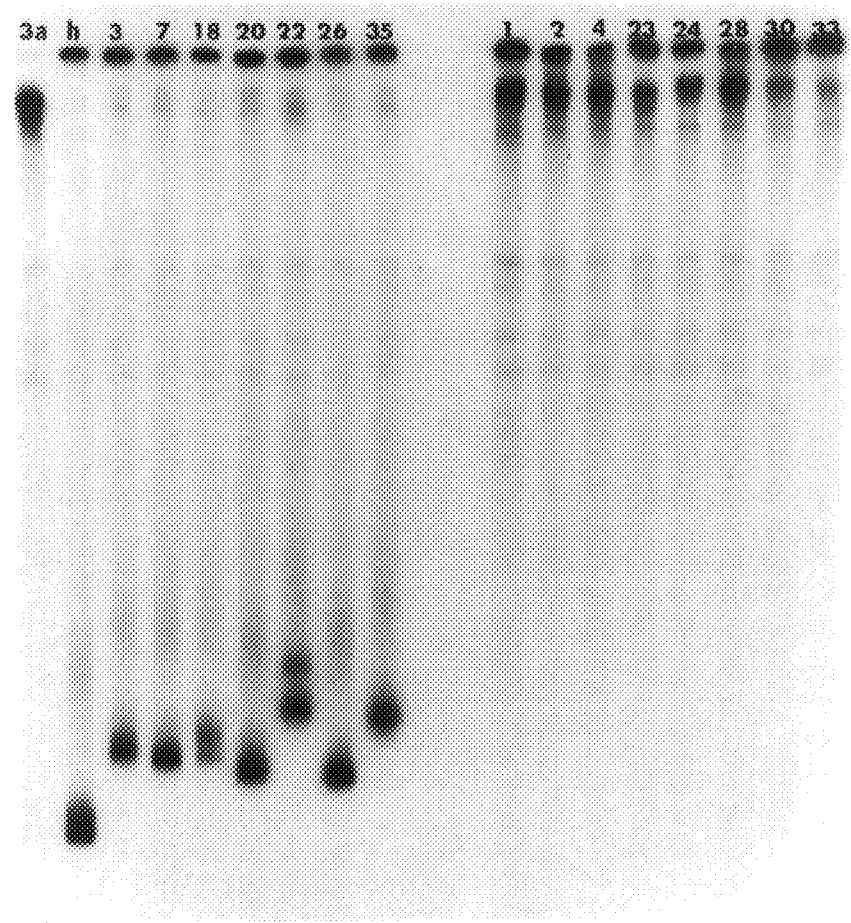

The ss probe 3a was derived from a plasmid clone of one RT-PCR product from a type 3a individual (JK3a), see FIG. 1E, lane h;) therefore, multiple bands in lane 22 most likely reflect two closely related viruses in this patient.

It appeared that most often patients had unique viral isolates. It is possible that patents 3 and 18 had identical or highly related virus isolates. Similarly, patients 20 and 26 had the same type 3a viral isolate and patients 2 and 4 has the same type 1b isolate based on the co-migration of the bands on MDE gels.

Figure 2A:
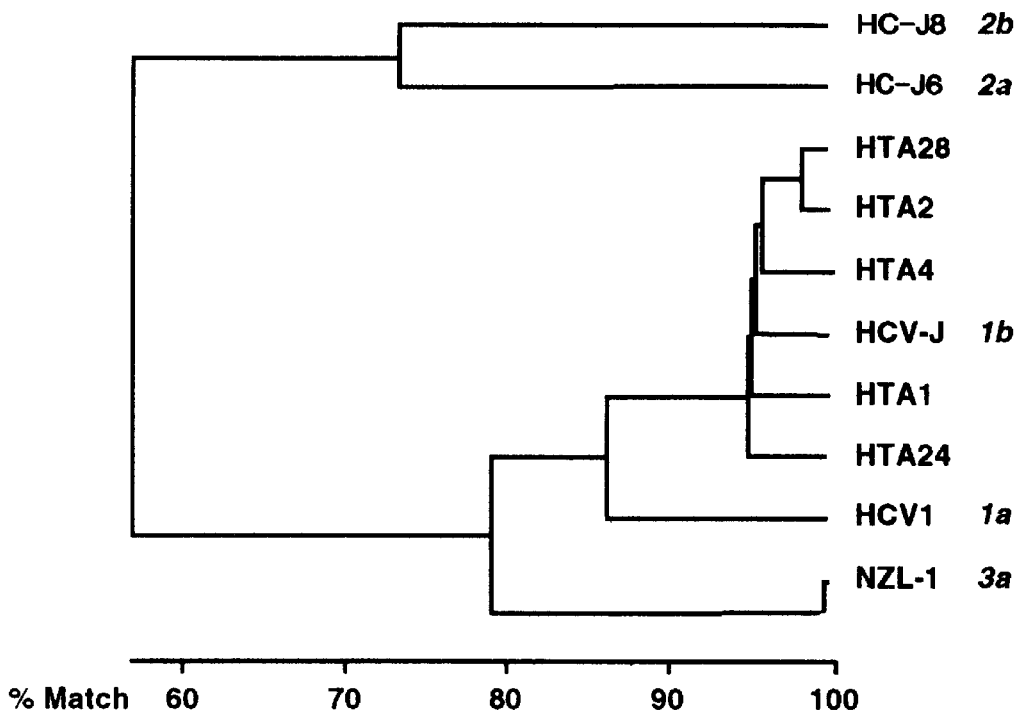
FIGS. 2A–2C are dendograms, i.e., phylogenetic trees showing the relatedness of each partial E1 nucleotide sequence, formed by comparing partial E1 sequences obtained by sequencing of putative type 1 (nt 625–930), type 2 (nt 583–915) or type 3 (nt 558–834) isolates from the dialysis patients described hereinto published genotype sequences for type 1a (HCV-1) (Choo, et al, PNAS (1991) 88:2451–2455, all nucleotide, "nt", designations according to this paper), 1b (HCV-J) (Kato et al, PNAS (1990) 87:9524–2528), 2a (HC-J6) (Okamoto et al Virol. (1992) 188:331–341), 2b (HC-J8) (Okamoto et al Virol. (1992) 188:331–341), 2c (Bukh, et al PNAS (1993) 90:8234–8239) and 3a (NZL-1) (Sakamoto, et al) *J. Gen. Virol.* (1994) 75:1761–1768 over the same region of the genome.
Figure 2B:
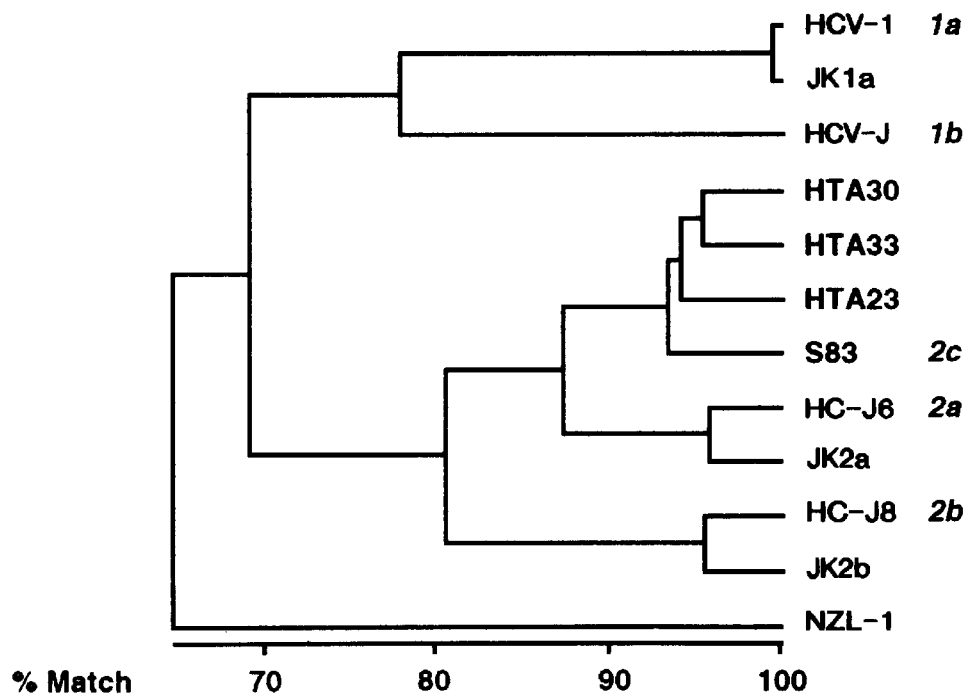
Figure 2C:
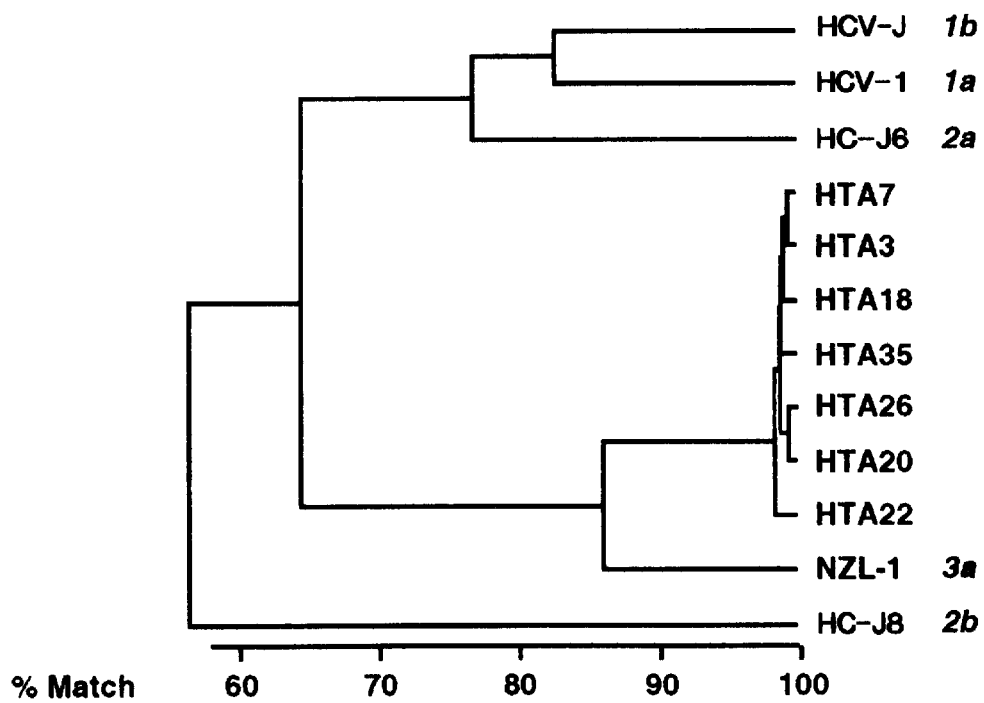

FIGS. 2A–2C depict phylogenetic trees, dendrograms, showing the genetic relatedness of each of the partial E1 nucleotide sequences. These denrograms were constructed by pairwise progressive alignment of the nucleotide sequences to one another by using the computer software program GeneWorks Unweighted Pair Group Methods with Arithmetic mean, as described in Weiner, et al., *J. Virol.* 67: pg. 4365–4368 (1993). The dendrograms, in FIGS. 2a–2c were formed by comparing partial E1 sequences of putative type 1 (nt 625–93), type 2 (nt 583–915) or type 3 (nt 558–834) isolates from the dialysis patients, as determined by sequence comparison to published genotype sequences for type 1a (HCV-1) (Choo, et al. PNAS 1991); 1b (HCV-J) (Kato et al).; 2a (HC-J6)(Okamoto, et al (1992); 2b (HC-J8)(Okamoto, et al, 1992); 2c (Bukh, et al.PNAS 1993) and 3a (NZL-1) (Sakamoto, et al. 1994) over the same region of the genome.

Figure 2D:
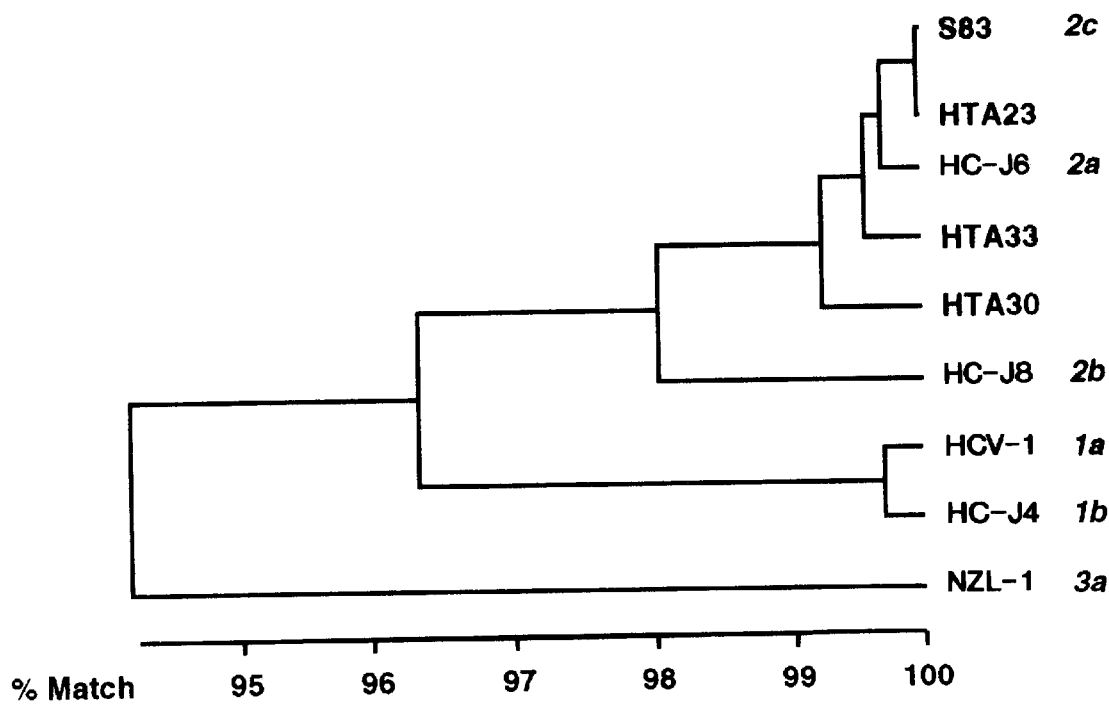
FIG. 2D is a dendogram, phylogenetic tree, formed by comparing either partial 5'UTR sequences of isolates 23, 30 and 33 obtained by direct sequencing with published type 1, 2 and 3 (nt –274 to –81) genotype sequences for the same region of the genome.

FIG. 2D is a dendrogram formed as described above by comparing either partial 5' UTR sequences of isolates 23, 30 and 33 with published type 1, 2 and 3 (nt–274 to –81) genotype sequences for the same region of the genome.

The results of the RFLP and HTA were compared and are presented in Table 2.

TABLE 2

Comparison of Partial E1 HTA and RFLP Genotyping Results

| Patient | HTA | RFLP |
|---------|-----|------|
| 1 | 1b | 1b |
| 2 | 1b | 1b |
| 3 | 3a | 3a |
| 4 | 1b | 1b |
| 7 | 3a | 3a |
| 18 | 3a | 3a |
| 20 | 3a | 3a |
| 22 | 3a | 3a |
| 23 | 2?* | 2a |
| 24 | 1b | 1b |
| 26 | 3a | 3a |
| 28 | 1b | 1b |
| 30 | 2?* | 2a |
| 33 | 2?* | 2a |
| 35 | 3a | 3a |

*sample is neither 2a nor 2b

The partial E1 sequences depicted in FIGS. 3a–3d confirm the HTA sub-type designations given in Table 2 and definitively show that patients 23, 30 and 33 are most closely related to 2c with 33 being the most distantly related to 2c. (18.6% divergent).

The RFLP results using ScrFI (see Davidson, et al., J. Gen. Virol. (1995) 76:1197–1204) wrongly designated 23, 30 and 33 as type 2a. This wrong designation is reflected in FIG. 2D which shows that based on the 5' UTR nt sequence, the computer did not accurately sub-type HCV 2c due to insufficient nt divergence in this region of the genome.

The present invention of HTA utilizing primers for the core and envelope region allowed for 3 levels of characterization of HCV genomes. The first was type specificity in the choice of RT-PCR primers. The second was sub-type specificity, based on choosing primers in the core/E1 region, and from a region greater than 400 nt, which resulted in a lack of cross-hybridization between sub-type probes, e.g. 1 and 3, 2a, 2b; and a high degree of heterogeneity to maximize differences between genotypes (lack of cross-hybridization). Finally, isolate specificity was determined by the distance from the homoduplex as exemplified in FIGS. 1.A–1-E. Other genotyping methods do not have the ability to analyze isolate differences.

What is claimed is:

1. An oligonucleotide consisting of the sequence of Seq ID No. 1.

2. An oligonucleotide consisting of the sequence of Seq ID No. 2.

3. An oligonucleotide consisting of the sequence of Seq ID No. 3.

4. An oligonucleotide consisting of the sequence of Seq ID No. 4.

5. An oligonucleotide consisting of the sequence of Seq ID No. 5.

6. An oligonucleotide consisting of the sequence of Seq ID No. 6.

7. An oligonucleotide consisting of the sequence of Seq ID No. 7.

8. An oligonucleotide consisting of the sequence of Seq ID No. 8.

9. An oligonucleotide consisting of the sequence of Seq ID No. 9.

10. A pair of PCR primers wherein the sense primer consists of Seq ID NO. 1 and the antisense primer is selected from the group consisting of Seq ID NO 2, Seq ID NO. 3, Seq ID NO. 4 and Seq ID NO. 5.

11. A pair of PCR primers wherein the antisense primer consists of Seq ID NO. 6 and the sense primer is selected from the group consisting of Seq ID NO 7, Seq ID NO. 8, and Seq ID NO. 9.

12. A method of determining the HCV genotype of an HCV strain, said method comprising the steps of:
(a) subjecting said HCV strain to one or more stages of PCR, wherein the one or more stages of PCR utilizes a sense probe from the core region of the HCV genome and an antisense probe from the E1 region of the HCV genome, or a sense probe from the E1 region of the HCV genome and an antisense probe from the core region of the HCV genome;
(b) forming a heteroduplex by denaturing and reannealing mixtures of the amplified product obtained in step (a) with DNA or RNA fragments of a known HCV genotype, said fragments comprising a region of the HCV genome between the core and E1 regions;
(c) comparing the mobility of said heteroduplex on a system that separates by size with the mobility of a homoduplex of the DNA or RNA fragments of known genotype to determine the genotype of the HCV strain.

13. The method of claim 12 wherein said HCV strain is subjected to two stages of PCR, wherein the first set of primers comprise a universal sense probe from the core or E1 regions of the HCV genome and a type specific antisense probe from the core or E1 regions of the HCV genome, and wherein the second set of PCR primers comprise a universal antisense probe from the core or E1 regions of the HCV genome and a type specific sense probe from the core or E1 regions of the HCV genome.

14. The method of claim 13 wherein the first set of PCR primers is comprised of the sense primer of SEQ ID NO: 1 and an antisense primer selected from the group consisting of SEQ ID NO: 2, SEQ ID NO: 3, SEQ ID NO: 4, and SEQ ID NO: 5, and wherein the second set of PCR primers is comprised of the antisense primer of SEQ ID NO: 6 and a sense primer selected from the group consisting of SEQ ID NO: 7, SEQ ID NO: 8, and SEQ ID NO: 9.

15. The method of claim 12 wherein said DNA or RNA fragments of known genotype comprise a DNA probe.

16. The method of claim 15 wherein said probe is single stranded.

17. The method of claim 16 wherein said DNA probe is radiolabeled.

18. The method of claim 16 wherein said single standed DNA probe is obtained by PCR amplification.

19. The method of claim 18 wherein said DNA probe is obtained by two step PCR amplification utilizing the sense primer of SEQ ID NO: 1 and an antisense primer selected from the group consisting of SEQ ID NO: 2, SEQ ID NO: 3, SEQ ID NO: 4, and SEQ ID NO: 5 for the first step, and the antisense primer of SEQ ID NO: 6 and a sense primer selected from the group consisting of SEQ ID NO: 7, SEQ ID NO: 8, and SEQ ID NO: 9 for the second step.

20. The method of claim 12 wherein said HCV strain is present in an excess in the mixture forming the heteroduplex.

21. A method to predict the response to drug therapy of a strain of HCV from a patient infected with said strain of HCV, said method comprising determining the sensitivity of known HCV genotypes to said drug therapy, determining the HCV genotype of said strain of HCV by the method according to claim 12, and comparing said HCV genotype of said strain prior to said drug therapy with said sensitivity of known HCV genotypes to said drug therapy, wherein said comparision is predictive of the response of said HCV strain to said drug therapy.

22. A method to predict the response to a therapeutic vaccine of a strain of HCV from a patient infected with said strain of HCV, said method comprising determining the sensitivity of known HCV genotypes to said therapeutic vaccine, determining the HCV genotype of said strain of HCV by the method according to claim 12, and comparing said HCV genotype of said strain prior to administration of said therapeutic vaccine with said sensitivity of known HCV genotypes to said therapeutic vaccine, wherein said comparision is predictive of the response of said HCV strain to said therapeutic vaccine.

23. A method to predict the appropriateness of a prophylactic vaccine composition for a given sample population, said method comprising determining the HCV genotype of the strain of said prophylactic vaccine, determining the predominance of known HCV genotypes in said sample population by the method according to claim 12, and comparing said HCV genotype of said prophylactic vaccine strain to the determined predominate HCV genotype in the sample population prior to administration of said prophylactic vaccine to said population sample, wherein said comparision is used to select a prophylactic vaccine of a strain likely to be prevalent in said population sample.

* * * * *

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCTGGTTGCT CTTTCTCTAT CT        22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATGGCTTGT GGGATCCGGA G        21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GATGACCTCG GGGACGCGCA T        21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GACCAGTTCT GGAACACGAG C        21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CAAGGTCTGG GGTAAACGCA G 21

(2) INFORMATION FOR SEQ ID NO:6:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:6:

CCAGTTCATC ATCATATCCC A 21

(2) INFORMATION FOR SEQ ID NO:7:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:7:

TGGCCCTGCT CTCTTGCTTG AC 22

(2) INFORMATION FOR SEQ ID NO:8:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:8:

TTGCTCTTCT GTCGTGCGTC AC 22

(2) INFORMATION FOR SEQ ID NO:9:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:9:

TTGCTCTGTT CTCTTGCTTA AT 22

(2) INFORMATION FOR SEQ ID NO:10:

(i) SEQUENCE CHARACTERISTICS:
  (A) LENGTH: 306 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:10:

AACTCAAGCA TTGTGTATGA AGCGGCGGAC ATGATCATGC ACACCCCGG GTGCGTGCCA 60

TGCGTCCGGG AGGGCAATCT CTCCCGCTGC TGGGTAGCGC TCACTCCCAC GCTCGCGGCC 120

AGAAACAGCA GCGTTCCTAC TACGACAATA CGACGCCATG TCGACTTGCT AGTAGGAGCG 180

| GCTGCTTTTT | GCTCCGCCAT | GTACGTGGGG | GACCTCTGCG | GATCTATTTT | CCTCGTCTCC | 240 |
| CAACTGTTCA | CCTTCTCGCC | CCGCCGGCAT | CATACAGTAC | AGGACTGCAA | TTGCTCGATC | 300 |
| TATCCC | | | | | | 306 |

( 2 ) INFORMATION FOR SEQ ID NO:11:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| AACTCAAGCA | TCGTGTATGA | GGCAGCGGAA | GTGATCATGC | ACATTCCCGG | GTGCGTGCCC | 60 |
| TGCGTTCGGG | AGAGCAATCT | CTCCCGCTGC | TGGGTAGCGC | TCACCCCCAC | ACTCGCGGCC | 120 |
| AGGAACAGCA | GCGTCCCCAC | CACGACAATA | CGACGCCACG | TCGACTTGCT | CGTTGGGGCG | 180 |
| GCTGCCTTCT | GCTCCGCTAT | GTATGTGGGG | GATCTCTGCG | GATCTGTTTT | CCTTGTCTCC | 240 |
| CAACTGTTCA | CCTTTTCGCC | TCGCCGGCAT | GAGACAGTAC | AGGACTGCAA | TTGTTCAATC | 300 |
| TATCCC | | | | | | 306 |

( 2 ) INFORMATION FOR SEQ ID NO:12:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| AACTCAAGCA | TAGTATATGA | GGCAGCGGAC | ATAATCATGC | ATACCCCGG | GTGCGTGCCC | 60 |
| TGTGTTCGGG | AGGTCAACTC | CTCCCGCTGC | TGGGCAGCGC | TCACCCCTAC | GCTCGCGGCC | 120 |
| AGGAACTCCA | GCGTGCCCAC | TACGACAATA | CGACGCCACG | TCGACTTGCT | CGTTGGGGCG | 180 |
| GCTGCTTTCT | GCTCCGCTAT | GTACGTGGGG | GATCTATGCG | GATCTGTTCT | ACTTGTCTCT | 240 |
| CAGCTGTTCA | CCTTCTCACC | TCGCCGGCAC | GAGACAGTGC | AGGACTGCAA | TTGTTCAATC | 300 |
| TATCCC | | | | | | 306 |

( 2 ) INFORMATION FOR SEQ ID NO:13:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| AACACGAGCA | TTGTGTATGA | GGCAGCGGAC | TTGATCATGC | ACGTCCCCGG | GTGCGTGCCC | 60 |
| TGCGTTCGGG | AGGGCAACTC | CTCCCGATGC | TGGGTAGCGC | TCACTCCCAC | GATCGCGGCC | 120 |
| AGGAACAGCA | GTGTCCCCGT | TACGACCATA | CGACGCCACG | TCGATTTGCT | CGTTGGGGCG | 180 |
| GCTGCTCTTT | GCTCCGCCAT | GTACGTGGGG | GATCTCTGCG | GATCTGTCTT | CCTCGCTTCC | 240 |
| CAGTTGTTCA | CTTTCTCGCC | TCGCCAGCAT | CAGACGGTAC | AGGACTGCAA | CTGCTCAATC | 300 |

| | | | | | | |
|---|---|---|---|---|---|---|
| TATCCC | | | | | | 306 |

(2) INFORMATION FOR SEQ ID NO:14:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

| | | | | | | |
|---|---|---|---|---|---|---|
| AACTCAAGCA | TCGTGTATGA | GGCGGCGGAA | GTGATCATGC | ACATTCCTGG | GTGCGTGCCC | 60 |
| TGCGTTCGGG | AGGGCGACTT | CTCCCGCTGC | TGGGTAGCGC | TCACCCCCAC | ACTCGCGGCC | 120 |
| AGGAATAACA | GCGTCCCCAC | TACGACAATA | CGACGCCACG | TCGACTTGCT | CGTTGGGGCG | 180 |
| GCTGCCTTCT | GCTCCGCTAT | GTACGTGGGG | GATCTCTGCG | GATCTGTTTT | CCTTGTCTCC | 240 |
| CAACTGTTCA | CCTTTTCGCC | TCGCCGGCAT | GCGACAGTAC | AGGACTGCAA | TTGTTCAATC | 300 |
| TATCCC | | | | | | 306 |

(2) INFORMATION FOR SEQ ID NO:15:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

| | | | | | | |
|---|---|---|---|---|---|---|
| AACTCGAGTA | TTGTGTACGA | GGCGGCCGAT | GCCATCCTGC | ACACTCCGGG | GTGCGTCCCT | 60 |
| TGCGTTCGTG | AGGGCAACGC | CTCGAGGTGT | TGGGTGGCGA | TGACCCCTAC | GGTGGCCACC | 120 |
| AGGGATGGCA | AACTCCCCGC | GACGCAGCTT | CGACGTCACA | TCGATCTGCT | TGTCGGGAGC | 180 |
| GCCACCCTCT | GTTCGGCCCT | CTACGTGGGG | GACCTATGCG | GGTCTGTCTT | TCTTGTCGGC | 240 |
| CAACTGTTCA | CCTTCTCTCC | CAGGCGCCAC | TGGACGACGC | AAGGTTGCAA | TTGCTCTATC | 300 |
| TATCCC | | | | | | 306 |

(2) INFORMATION FOR SEQ ID NO:16:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

| | | | | | | |
|---|---|---|---|---|---|---|
| AACTCAAGTA | TTGTGTATGA | GGCAGCGGAC | ATGATCATGC | ACACCCCGG | GTGCGTGCCC | 60 |
| TGCGTCCGGG | AGAGTAATTT | CTCCCGTTGC | TGGGTAGCGC | TCACTCCCAC | GCTCGCGGCC | 120 |
| AGGAACAGCA | GCATCCCCAC | CACGACAATA | CGACGCCACG | TCGATTTGCT | CGTTGGGGCG | 180 |
| GCTGCTCTCT | GTTCCGCTAT | GTACGTTGGG | GATCTCTGCG | GATCCGTTTT | TCTCGTCTCC | 240 |
| CAGCTGTTCA | CCTTCTCACC | TCGCCGGTAT | GAGACGGTAC | AAGATTGCAA | TTGCTCAATC | 300 |
| TATCCC | | | | | | 306 |

(2) INFORMATION FOR SEQ ID NO:17:

( i ) SEQUENCE CHARACTERISTICS:
 ( A ) LENGTH: 306 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| AATGATAGCA | TTACCTGGCA | ACTCCAGGCT | GCTGTCCTCC | ACGTCCCCGG | GTGCGTCCCG | 60 |
| TGCGAGAAAG | TGGGGAATAC | ATCTCGGTGC | TGGATACCGG | TCTCACCGAA | TGTGGCCGTG | 120 |
| CAGCAGCCCG | GCGCCCTCAC | GCAGGGCTTA | CGGACGCACA | TTGACATGGT | TGTGATGTCC | 180 |
| GCCACGCTCT | GCTCCGCTCT | TTACGTGGGG | GACCTCTGCG | GTGGGGTGAT | GCTTGCAGCC | 240 |
| CAGATGTTCA | TTGTCTCGCC | ACAGCACCAC | TGGTTTGTGC | AAGACTGCAA | TTGCTCCATC | 300 |
| TACCCT | | | | | | 306 |

( 2 ) INFORMATION FOR SEQ ID NO:18:

( i ) SEQUENCE CHARACTERISTICS:
  ( A ) LENGTH: 306 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| AACAACAGCA | TCACCTGGCA | GCTCACTGAC | GCAGTTCTCC | ATCTTCCTGG | ATGCGTCCCA | 60 |
| TGTGAGAATG | ATAATGGCAC | CTTGCATTGC | TGGATACAAG | TAACACCCAA | CGTGGCTGTG | 120 |
| AAACACCGCG | GTGCGCTCAC | TCGTAGCCTG | CGAACACACG | TCGACATGAT | CGTAATGGCA | 180 |
| GCTACGGCCT | GCTCGGCCTT | GTATGTGGGA | GATGTGTGCG | GGGCCGTGAT | GATTCTATCG | 240 |
| CAGGCTTTCA | TGGTATCACC | ACAACGCCAC | AACTTCACCC | AAGAGTGCAA | CTGTTCCATC | 300 |
| TACCAA | | | | | | 306 |

( 2 ) INFORMATION FOR SEQ ID NO:19:

( i ) SEQUENCE CHARACTERISTICS:
  ( A ) LENGTH: 306 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:19:

| | | | | | |
|---|---|---|---|---|---|
| AATAGCAGTA | TTGTGTATGA | GGCCGATGAT | GTCATTCTGC | ACACACCCGG | CTGTGTACCT | 60 |
| TGTGTCCAGG | ACGGCAATAC | ATCTACGTGC | TGGACCCCAG | TGACACCTAC | AGTGGCAGTC | 120 |
| AGGTACGTCG | GAGCAACTAC | TGCTTCGATA | CGCAGTCATG | TGGACCTATT | AGTAGGCGCG | 180 |
| GCCACGATGT | GCTCTGCGCT | CTACGTGGGT | GATATGTGTG | GGGCTGTCTT | TCTCGTGGGA | 240 |
| CAAGCCTTCA | CGTTCAGACC | TCGACGCCAT | CAAACGGTCC | AGACCTGTAA | CTGCTCGCTG | 300 |
| TACCCA | | | | | | 306 |

( 2 ) INFORMATION FOR SEQ ID NO:20:

( i ) SEQUENCE CHARACTERISTICS:
  ( A ) LENGTH: 333 base pairs
  ( B ) TYPE: nucleic acid
  ( C ) STRANDEDNESS: single
  ( D ) TOPOLOGY: linear (ii) MOLECULE TYPE: DNA (genomic)

(xi) SEQUENCE DESCRIPTION: SEQ ID NO:20:

| | | | | | | |
|---|---|---|---|---|---|---|
| CGCAACTCCA | CGGGGCTTTA | CCACGTCACC | AATGATTGCC | CTAACTCGAG | TATTGTGTAC | 60 |
| GAGACGGCCG | ATGCCATCCT | GCACACTCCG | GGGTGCGTCC | CTTGTGTTCG | CGAGGGCAAC | 120 |
| GCCTCGAGGT | GTTGGGTGGC | GATGACCCCT | ACGGTGGCCA | CCAGGGATGG | CAAACTCCCC | 180 |
| GCGACGCAGC | TTCGACGTCA | CATCGATCTG | CTTGTCGGGA | GCGCCACCCT | CTGTTCGGCC | 240 |
| CTCTACGTGG | GGGATCTGTG | CGGGTCTGTC | TTTCTTGTCG | GCCAACTGTT | TACCTTCTCT | 300 |
| CCCAGGCGCC | ACTGGACGAC | GCAAGGTTGC | AAT | | | 333 |

(2) INFORMATION FOR SEQ ID NO:21:

(i) SEQUENCE CHARACTERISTICS:
(A) LENGTH: 333 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

| | | | | | | |
|---|---|---|---|---|---|---|
| AAGAACACCA | GCGACAGCTA | CATGGTGACC | AATGACTGCC | AAAATGACAG | CATCACCTGG | 60 |
| CAGCTTGAGG | CTGCGGTCCT | CCACGTCCCC | GGGTGCGTCC | CGTGCGAGAG | AGTGGGAAAT | 120 |
| ACATCTCGGT | GCTGGATACC | GGTCTCACCA | AACGTGGCTG | TGCGGCAGCC | CGGCGCCCTC | 180 |
| ACGCAGGGCT | TGCGGACGCA | CATCGACATG | ATTGTGATGT | CCGCCACGCT | CTGCTCCGCT | 240 |
| CTCTACGTGG | GGGACCTCTG | TGGCGGGATG | ATGCTCGCAG | CCCAGATGTT | CATCGTTTCG | 300 |
| CCGCAGAACC | ACTGGTTCGT | GCAGGAATGC | AAT | | | 333 |

(2) INFORMATION FOR SEQ ID NO:22:

(i) SEQUENCE CHARACTERISTICS:
(A) LENGTH: 333 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

| | | | | | | |
|---|---|---|---|---|---|---|
| AGGAACATCA | GTTCTAGCTA | CTACGCCACT | AATGACTGCT | CGAACAACAG | CATCACCTGG | 60 |
| CAGCTCACCA | ACGCAGTTCT | CCACCTTCCC | GGATGCGTCC | CATGTGAGAA | TAATAATGGC | 120 |
| ACCTTGCATT | GCTGGATACA | AGTAACACCT | AATGTGGCCG | TAAAACATCG | CGGCGCACTC | 180 |
| ACTCACAACC | TGCGGACACA | TGTCGACATG | ATCGTAATGG | CAGCTACGGT | CTGTTCGGCC | 240 |
| TTGTACGTAG | GAGACGTGTG | TGGGGCTGTG | ATGATTGTGT | CTCAGGCCCT | TATAATATCA | 300 |
| CCAGAACACC | ATAACTTCAC | CCAAGAGTGC | AAC | | | 333 |

(2) INFORMATION FOR SEQ ID NO:23:

(i) SEQUENCE CHARACTERISTICS:
(A) LENGTH: 333 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

| | | | | | |
|---|---|---|---|---|---|
| AAGGACACCG | GCGACTCCTA | CATGCCGACC | AACGATTGCT | CCAACTCTAG | TATCGTTTGG | 60
| CAGCTTGAAG | GAGCAGTGCT | TCATACTCCT | GGATGCGTCC | CTTGTGAGCG | TACCGCCAAC | 120
| GTCTCTCGAT | GTTGGGTGCC | GGTTGCCCCC | AATCTCGCCA | TAAGTCAACC | TGGCGCTCTC | 180
| ACTAAGGGCC | TGCGAGCACA | CATCGATATC | ATCGTGATGT | CTGCTACGGT | CTGTTCTGCC | 240
| CTTTATGTGG | GGGACGTGTG | TGGCGCGCTG | ATGCTGGCCG | CTCAGGTCGT | CGTCGTGTCG | 300
| CCACAACACC | ATACGTTTGT | CCAGGAATGC | AAC | | | 333

( 2 ) INFORMATION FOR SEQ ID NO:24:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

| | | | | | |
|---|---|---|---|---|---|
| AAAAACACCA | GCATCTCCTA | TATGGCGACC | AACGACTGCT | CCAATTCCAG | CATCGCTTGG | 60
| CAGTTTGACG | GCGCAGTGCT | CCATACTCCT | GGATGTGTCC | CTTGCGAACG | GACCGGCAAC | 120
| GCGTCCCGGT | GTTGGGTGCC | GGTTGCCCCC | AATGTGGCTA | TAAGACAACC | CGGCGCCCTC | 180
| ACTAAGGGCA | TACGAACGCA | CATTGATGTC | ATCGTAATGT | CTGCTACGCT | CTGTTCTGCC | 240
| CTTTACGTGG | GGGACGTGTG | TGGTGCGCTG | ATGATTGCCG | CTCAGGTCGT | CATTGTGTCT | 300
| CCGCAGCATC | ACCACTTTGT | CCAGGACTGC | AAT | | | 333

( 2 ) INFORMATION FOR SEQ ID NO:25:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

| | | | | | |
|---|---|---|---|---|---|
| AAGAACACCA | GCGACTCCTA | CATGGCGACT | AACGACTGCT | CTAACTCCAG | CATCGTTTGG | 60
| CAGCTTGAGG | ACGCAGTGCT | CCATGTCCCT | GGATGTGTCC | CTTGTGAGAA | GACTGGCAAT | 120
| ACGTCTCGGT | GCTGGGTGCC | GGTTACCCCC | AATGTGGCTA | CAAGTCAACC | CGGCGCTCTC | 180
| ACCAGGGGCT | TGCGGACGCA | CATCGATGTC | ATCGTGATGT | CAGCCACGCT | CTGCTCCGCT | 240
| CTCTATGTGG | GGGACGTGTG | TGGCGCGTTG | ACGATAGCCG | CTCAGGTTGT | CATCGTATCG | 300
| CCACGGCACC | ACCACTTTGT | CCAGGACTGC | AAT | | | 333

( 2 ) INFORMATION FOR SEQ ID NO:26:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

| | | | | | |
|---|---|---|---|---|---|
| AAGAACACCA | GCACCTCCTA | CATGGTGACT | AACGATTGCT | CCAACTCCAG | CATCGTTTGG | 60
| CAACTTGAAG | GCGCAGTGCT | CCATGTTCCT | GGATGTGTCC | CTTGTGAGCA | GATCGGCAAC | 120
| GTGTCTCAGT | GTTGGGTGCC | GGTTACCCCC | AATATGGCCA | TAAGTACACC | CGGCGCTCTC | 180

```
ACTAAGGGCT  TGCGAACGCA  CATCGACGGC  ATCGTGATGT  CCGCTACGCT  CTGTTCTGCC      240

CTTTATGTGG  GGGACGTGTG  TGGCGCGTTG  ATGATAGCCG  CCCAGGTCGT  CATCGTATCG      300

CCACAGCACC  ACCACTTTGT  CCACGACTGC  AAC                                    333
```

( 2 ) INFORMATION FOR SEQ ID NO:27:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
CGCAACTCCA  CGGGGCTTTA  CCACGTCACC  AATGATTGCC  CTAACTCGAG  TATTGTGTAC       60

GAGGCGGCCG  ATGCCATCCT  GCACACTCCG  GGGTGCGTCC  CTTGCGTTCG  TGAGGGCAAC      120

GCCTCGAGGT  GTTGGGTGGC  GATGACCCCT  ACGGTGGCCA  CCAGGGATGG  CAAACTCCCC      180

GCGACGCAGC  TTCGACGTCA  CATCGATCTG  CTTGTCGGGA  GCGCCACCCT  CTGTTCGGCC      240

CTCTACGTGG  GGGACCTATG  CGGGTCTGTC  TTTCTTGTCG  GCCAACTGTT  CACCTTCTCT      300

CCCAGGCGCC  ACTGGACGAC  GCAAGGTTGC  AAT                                    333
```

( 2 ) INFORMATION FOR SEQ ID NO:28:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CGCAACGTGT  CCGGGATATA  CCATGTCACG  AACGACTGCT  CCAACTCAAG  TATTGTGTAT       60

GAGGCAGCGG  ACATGATCAT  GCACACCCCC  GGGTGCGTGC  CCTGCGTCCG  GGAGAGTAAT      120

TTCTCCCGTT  GCTGGGTAGC  GCTCACTCCC  ACGCTCGCGG  CCAGGAACAG  CAGCATCCCC      180

ACCACGACAA  TACGACGCCA  CGTCGATTTG  CTCGTTGGGG  CGGCTGCTCT  CTGTTCCGCT      240

ATGTACGTTG  GGGATCTCTG  CGGATCCGTT  TTTCTCGTCT  CCCAGCTGTT  CACCTTCTCA      300

CCTCGCCGGT  ATGAGACGGT  ACAAGATTGC  AAT                                    333
```

( 2 ) INFORMATION FOR SEQ ID NO:29:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
AGGAACATTA  GTTCTAGCTA  CTACGCCACT  AATGATTGCT  CAAACAACAG  CATCACCTGG       60

CAGCTCACTG  ACGCAGTTCT  CCATCTTCCT  GGATGCGTCC  CATGTGAGAA  TGATAATGGC      120

ACCTTGCATT  GCTGGATACA  AGTAACACCC  AACGTGGCTG  TGAAACACCG  CGGTGCGCTC      180

ACTCGTAGCC  TGCGAACACA  CGTCGACATG  ATCGTAATGG  CAGCTACGGC  CTGCTCGGCC      240

TTGTATGTGG  GAGATGTGTG  CGGGGCCGTG  ATGATTCTAT  CGCAGGCTTT  CATGGTATCA      300
```

CCACAACGCC ACAACTTCAC CCAAGAGTGC AAC 333

( 2 ) INFORMATION FOR SEQ ID NO:30:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CGGAATACGT CTGGCCTCTA CGTCCTTACC AACGACTGTT CCAATAGCAG TATTGTGTAT 60

GAGGCCGATG ATGTCATTCT GCACACACCC GGCTGTGTAC CTTGTGTCCA GGACGGCAAT 120

ACATCTACGT GCTGGACCCC AGTGACACCT ACAGTGGCAG TCAGGTACGT CGGAGCAACT 180

ACTGCTTCGA TACGCAGTCA TGTGGACCTA TTAGTAGGCG CGGCCACGAT GTGCTCTGCG 240

CTCTACGTGG GTGATATGTG TGGGGCTGTC TTTCTCGTGG GACAAGCCTT CACGTTCAGA 300

CCTCGACGCC ATCAAACGGT CCAGACCTGT AAC 333

( 2 ) INFORMATION FOR SEQ ID NO:31:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AAGAACATCA GTACCGGCTA CATGGTGACC AACGACTGCA CCAATGATAG CATTACCTGG 60

CAACTCCAGG CTGCTGTCCT CCACGTCCCC GGGTGCGTCC CGTGCGAGAA AGTGGGAAT 120

ACATCTCGGT GCTGGATACC GGTCTCACCG AATGTGGCCG TGCAGCAGCC CGGCGCCCTC 180

ACGCAGGGCT TACGGACGCA CATTGACATG GTTGTGATGT CCGCCACGCT CTGCTCCGCT 240

CTTTACGTGG GGGACCTCTG CGGTGGGGTG ATGCTTGCAG CCCAGATGTT CATTGTCTCG 300

CCACAGCACC ACTGGTTTGT GCAAGACTGC AAT 333

( 2 ) INFORMATION FOR SEQ ID NO:32:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TCATCCAACA TCTAGTCTAG AGTGGCGGAA TACGTCTGGC CTCTATGTCC TTACCAACGA 60

CTGTTCCAAT AACATTATTG TGTATGAGGC CGATGACGTC ATCCTGCACA CGCCCGGCTG 120

TGTACCTTGT GTTCAGGACG GTAATACATC CAAGTGCTGG ACCCAGTGA CACCTACAGT 180

GGCAGTCAGG TACGTCGGAG CAACCACCGC TTCAATACGC AGCCACGTGG ACCTATTATT 240

GGGCGCGGCC ACGATGTGCT CTGCGCTCTA CGTGGGT 277

( 2 ) INFORMATION FOR SEQ ID NO:33:

( i ) SEQUENCE CHARACTERISTICS:
        ( A ) LENGTH: 277 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

| | | | | | |
|---|---|---|---|---|---|
| TCATCCAACA | TCTAGTCTAG | AGTGGCGGAA | TACGTCTGGC | CTCTATGTCC | TTACCAACGA | 60
| CTGTTCCAAT | AACATCATTG | TGTATGAGGC | CGATGACGTC | ATCCTGCACG | CACCCGGCTG | 120
| TGTACCTTGT | GTTCAGGACG | GCAATACATC | CACGTGCTGG | ACCCCAGTGA | CACCTACAGT | 180
| GGCAGTCAGG | TACGTCGGAG | CAACCACCGC | TTCAATACGC | AGCCATGTGG | ACCTATTAGT | 240
| GGGCGCGGCC | ACGATGTGCT | CTGCGCTCTA | CGTGGGT | | | 277

(2) INFORMATION FOR SEQ ID NO:34:

(i) SEQUENCE CHARACTERISTICS:
(A) LENGTH: 277 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

| | | | | | |
|---|---|---|---|---|---|
| TCATCCAACA | TCTAGTCTAG | AGTGGCGGAA | TACGTCTGGC | CTCTATGTCC | TTACCAACGA | 60
| CTGTTCCAAT | AATATTATTG | TGTATGAGGC | CGACGACGTC | ATCCTGCACG | CCCCCGGCTG | 120
| TGTACCTTGT | GTTCAGGACG | GCAATACATC | CACGTGCTGG | ATCCCAGTGA | CACCTACAGT | 180
| GGCAGTCAGG | TACGCCGGAG | CAACCACCGC | TTCAATACGC | AGCCATGTGG | ACCTGTTAGT | 240
| GGGCGCGGCC | ACGATGTGCT | CTGCGCTCTA | CGTGGGT | | | 277

(2) INFORMATION FOR SEQ ID NO:35:

(i) SEQUENCE CHARACTERISTICS:
(A) LENGTH: 277 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

| | | | | | |
|---|---|---|---|---|---|
| TCATCCAACA | TCTAGTCTAG | AGTGGCGGAA | TACGTCTGGC | CTCTATGTCC | TTACCAACGA | 60
| CTGTTCCAAT | AACATTATTG | TGTATGAGGC | CGATGACGTC | ATCCTGCACA | CACCCGGCTG | 120
| TGTACCTTGT | GTTCAGGACG | GCAATACATC | CACGTGCTGG | ACCCCAGTGA | CACCTACAGT | 180
| ATCAGTCAGG | TACGTCGGAG | CAACCACCGC | TTCAATACGC | AGCCATGTGG | ACCTACTATT | 240
| GGGCGCGGCC | ACGATGTGCT | CCGCGCTCTA | CGTGGGT | | | 277

(2) INFORMATION FOR SEQ ID NO:36:

(i) SEQUENCE CHARACTERISTICS:
(A) LENGTH: 277 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

| | | | | | |
|---|---|---|---|---|---|
| TCATCCAACA | TCTAGTCTAG | AGTGGCGGAA | TACGTCTGGC | CTCTATGTCC | TTACCAACGA | 60
| CTGTTCCAAT | AACAGTATTG | TGTATGAGGC | CGATCACGTC | ATCCTGCACA | CACCCGGCTG | 120

```
TGTACCTTGT GTTCAAGCCA ACAATAAATC CAAATGCTGG ACCCCAGTGA CACCTACAGT      180

ATCAGTCGAG TACGTCGGAG CAACCACCGC TTCAATACGC AGCCATGTGG ACCTACTATT      240

GGGCGCGGCC ACGATGTGCT CTGCGCTCTA CGTGGGT                               277
```

( 2 ) INFORMATION FOR SEQ ID NO:37:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

```
TCATCCAACA TCTAGTCTAG AGTGGCGGAA TACGTCTGGC CTCTATGTCC TTACCAACGA       60

CTGTTCTAAT AACATTATTG TGTATGAGGC CGATGACGTC ATCCTGCACA CACCCGGCTG      120

TGTACCTTGT GTTCAGGACG GCAATGCATC CACGTGCTGG ACCCCAGTAA CACCTACAGT      180

ATCAGTCAGG TACGTCGGAG CAACCACCGC TTCAGTACGC AGCCATGTGG ACCTACTATT      240

GGGCGCGGCC ACGATGTGCT CTGCGCTCTA TGTGGGT                               277
```

( 2 ) INFORMATION FOR SEQ ID NO:38:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

```
TCATCCAACA TCTAGTCTAG AGTGGCGGAA TACGTCTGGC CTCTATGTCC TCACCAACGA       60

CTGTTCCAAC AACATTATTG TGTATGAGGC CGATGACGTC ATTCTGCACA CGCCCGGCTG      120

CGTACCTTGT GTACAGGACG GCAATACATC CACGTGCTGG ACCCCAGTGA CACCTACAGT      180

GGCAGTCAGG TACGTCGGAG CAACTACCGC TTCAATACGC AGCCATGTGG ACCTATTATT      240

GGGCGCGGCC ACGATGTGCT CTGCGCTCTA CGTGGGT                               277
```

( 2 ) INFORMATION FOR SEQ ID NO:39:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

```
TCATCCAGCA GCCAGTCTAG AGTGGCGGAA TACGTCTGGC CTCTACGTCC TTACCAACGA       60

CTGTTCCAAT AGCAGTATTG TGTATGAGGC CGATGATGTC ATTCTGCACA CACCCGGCTG      120

TGTACCTTGT GTCCAGGACG GCAATACATC TACGTGCTGG ACCCCAGTGA CACCTACAGT      180

GGCAGTCAGG TACGTCGGAG CAACTACTGC TTCGATACGC AGTCATGTGG ACCTATTAGT      240

AGGCGCGGCC ACGATGTGCT CTGCGCTCTA CGTGGGT                               277
```

( 2 ) INFORMATION FOR SEQ ID NO:40:

( i ) SEQUENCE CHARACTERISTICS:

(A) LENGTH: 277 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:40:

| | | | | | |
|---|---|---|---|---|---|
| TGTGCCCGCT | TCGGCCTACC | AAGTGCGCAA | CTCCACGGGG | CTTTACCACG | TCACCAATGA | 60
| TTGCCCTAAC | TCGAGTATTG | TGTACGAGGC | GGCCGATGCC | ATCCTGCACA | CTCCGGGGTG | 120
| CGTCCCTTGC | GTTCGTGAGG | GCAACGCCTC | GAGGTGTTGG | GTGGCGATGA | CCCCTACGGT | 180
| GGCCACCAGG | GATGGCAAAC | TCCCCGCGAC | GCAGCTTCGA | CGTCACATCG | ATCTGCTTGT | 240
| CGGGAGCGCC | ACCCTCTGTT | CGGCCCTCTA | CGTGGGG | | | 277

(2) INFORMATION FOR SEQ ID NO:41:

(i) SEQUENCE CHARACTERISTICS:
(A) LENGTH: 277 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:41:

| | | | | | |
|---|---|---|---|---|---|
| CATCCCAGCT | TCCGCTTACG | AGGTGCGCAA | CGTGTCCGGG | ATATACCATG | TCACGAACGA | 60
| CTGCTCCAAC | TCAAGTATTG | TGTATGAGGC | AGCGGACATG | ATCATGCACA | CCCCCGGGTG | 120
| CGTGCCCTGC | GTCCGGGAGA | GTAATTTCTC | CCGTTGCTGG | GTAGCGCTCA | CTCCCACGCT | 180
| CGCGGCCAGG | AACAGCAGCA | TCCCCACCAC | GACAATACGA | CGCCACGTCG | ATTTGCTCGT | 240
| TGGGGCGGCT | GCTCTCTGTT | CCGCTATGTA | CGTTGGG | | | 277

(2) INFORMATION FOR SEQ ID NO:42:

(i) SEQUENCE CHARACTERISTICS:
(A) LENGTH: 277 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:42:

| | | | | | |
|---|---|---|---|---|---|
| CACCCCGGTC | TCCGCTGCCG | AAGTGAAGAA | CATCAGTACC | GGCTACATGG | TGACCAACGA | 60
| CTGCACCAAT | GATAGCATTA | CCTGGCAACT | CCAGGCTGCT | GTCCTCCACG | TCCCCGGGTG | 120
| CGTCCCGTGC | GAGAAAGTGG | GGAATACATC | TCGGTGCTGG | ATACCGGTCT | CACCGAATGT | 180
| GGCCGTGCAG | CAGCCCGGCG | CCCTCACGCA | GGGCTTACGG | ACGCACATTG | ACATGGTTGT | 240
| GATGTCCGCC | ACGCTCTGCT | CCGCTCTTTA | CGTGGGG | | | 277

(2) INFORMATION FOR SEQ ID NO:43:

(i) SEQUENCE CHARACTERISTICS:
(A) LENGTH: 277 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:43:

| | | | | | |
|---|---|---|---|---|---|
| AGTGCCAGTG | TCTGCAGTGG | AAGTCAGGAA | CATTAGTTCT | AGCTACTACG | CCACTAATGA | 60

| | | | | | |
|---|---|---|---|---|---|
|TTGCTCAAAC|AACAGCATCA|CCTGGCAGCT|CACTGACGCA|GTTCTCCATC|TTCCTGGATG|120|
|CGTCCCATGT|GAGAATGATA|ATGGCACCTT|GCATTGCTGG|ATACAAGTAA|CACCCAACGT|180|
|GGCTGTGAAA|CACCGCGGTG|CGCTCACTCG|TAGCCTGCGA|ACACACGTCG|ACATGATCGT|240|
|AATGGCAGCT|ACGGCCTGCT|CGGCCTTGTA|TGTGGGA| | |277|

( 2 ) INFORMATION FOR SEQ ID NO:44:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

| | | | | | |
|---|---|---|---|---|---|
|GCAGAAAGCG|TCTAGCCATG|GCGTTAGTAT|GAGTGTCGTA|CAGCCTCCAG|GCCCCCCCT|60|
|CCCGGGAGAG|CCATAGTGGT|CTGCGGAACC|GGTGAGTACA|CCGGAATTGC|CGGGAAGACT|120|
|GGGTCCTTTC|TTGGATAAAC|CCACTCTATG|CCCGGTCATT|TGGGCGTGCC|CCCGCAAGAC|180|
|TGCTAGCCGA|GTAG| | | |194|

( 2 ) INFORMATION FOR SEQ ID NO:45:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

| | | | | | |
|---|---|---|---|---|---|
|GCAGAAAGCG|TCTAGCCATG|GCGTTAGTAT|GAGTGTCGTA|CAGCCTCCAG|GCCCCCCCT|60|
|CCCGGGAGAG|CCATAGTGGT|CTGCGGAACC|GGTGAGTACA|CCGGAATTAC|CGGAAAGACT|120|
|GGGTCCTTTC|TTGGATAAAC|CCACTCTATG|TCCGGTCATT|TGGGCACGCC|CCCGCAAGAC|180|
|TGCTAGCCGA|GTAG| | | |194|

( 2 ) INFORMATION FOR SEQ ID NO:46:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

| | | | | | |
|---|---|---|---|---|---|
|GCAGAAAGCG|TCTAGCCATG|GCGTTAGTAT|GAGTGTCGTG|CAGCCTCCAG|GACCCCCCT|60|
|CCCGGGAGAG|CCATAGTGGT|CTGCGGAACC|GGTGAGTACA|CCGGAATTGC|CAGGACGACC|120|
|GGGTCCTTTC|TTGGATCAAC|CCGCTCAATG|CCTGGAGATT|TGGGCGTGCC|CCCGCGAGAC|180|
|TGCTAGCCGA|GTAG| | | |194|

( 2 ) INFORMATION FOR SEQ ID NO:47:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

```
GCAGAAAGCG  TCTAGCCATG  GCGTTAGTAT  GAGTGTCGTG  CAGCCTCCAG  GACCCCCCCT        60
CCCGGGAGAG  CCATAGTGGT  CTGCGGAACC  GGTGAGTACA  CCGGAATTGC  CAGGACGACC       120
GGGTCCTTTC  TTGGATCAAC  CCGCTCAATG  CCTGGAGATT  TGGGCGTGCC  CCCGCAAGAC       180
TGCTAGCCGA  GTAG                                                             194
```

( 2 ) INFORMATION FOR SEQ ID NO:48:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
GCGGAAAGCG  CCTAGCCATG  GCGTTAGTAC  GAGTGTCGTG  CAGCCTCCAG  GACCCCCCCT        60
CCCGGGAGAG  CCATAGTGGT  CTGCGGAACC  GGTGAGTACA  CCGGAATCGC  TGGGGTGACC       120
GGGTCCTTTC  TTGGAGCAAC  CCGCTCAATA  CCCAGAAATT  TGGGCGTGCC  CCCGCGAGAT       180
CACTAGCCGA  GTAG                                                             194
```

( 2 ) INFORMATION FOR SEQ ID NO:49:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

```
GCAGAAAGCG  TCTAGCCATG  GCGTTAGTAT  GAGTGTCGTA  CAGCCTCCAG  GCCCCCCCT         60
CCCGGGAGAG  CCATAGTGGT  CTGCGGAACC  GGTGAGTACA  CCGGAATTGC  CGGGAAGACT       120
GGGTCCTTTC  TTGGATAAAC  CCACTCTATG  CCCGGCCATT  TGGGCGTGCC  CCCGCAAGAC       180
TGCTAGCCGA  GTAG                                                             194
```

( 2 ) INFORMATION FOR SEQ ID NO:50:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

```
GCAGAAAGCG  TCTAGCCATG  GCGTTAGTAT  GAGTGTCGTA  CAGCCTCCAG  GCCCCCCCT         60
CCCGGGAGAG  CCATAGTGGT  CTGCGGAACC  GGTGAGTACA  CCGGAATTGC  CGGGAAGACT       120
GGGTCCTTTC  TTGGATAAAC  CCACTCTATG  CCCGGCCATT  TGGGCGTGCC  CCCGCAAGAC       180
TGCTAGCCGA  GTAG                                                             194
```

( 2 ) INFORMATION FOR SEQ ID NO:51:

( i ) SEQUENCE CHARACTERISTICS:
        ( A ) LENGTH: 194 base pairs

-continued ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:51:

| | | | | | | |
|---|---|---|---|---|---|---|
| GCAGAAAGCG | TCTAGCCATG | GCGTTAGTAT | GAGTGTCGTA | CAGCCTCCAG | GCCCCCCCT | 60 |
| CCCGGGAGAG | CCATAGTGGT | CTGCGGAACC | GGTGAGTACA | CCGGAATTGC | CAGGAAGACT | 120 |
| GGGTCCTTTC | TTGGATAAAC | CCACTCTATG | CCTGGCCATT | TGGGCGTGCC | CCCGCAAGAC | 180 |
| TGCTAGCCGA | GTAG | | | | | 194 |

( 2 ) INFORMATION FOR SEQ ID NO:52:

( i ) SEQUENCE CHARACTERISTICS:
( A ) LENGTH: 194 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:52:

| | | | | | | |
|---|---|---|---|---|---|---|
| GCAGAAAGCG | TCTAGCCATG | GCGTTAGTAT | GAGTGTCGTA | CAGCCTCCAG | GTCCCCCCT | 60 |
| CCCGGGAGAG | CCATAGTGGT | CTGCGGAACC | GGTGAGTACA | CCGGAATTGC | CGGGAAGACT | 120 |
| GGGTCCTTTC | TTGGATAAAC | CCACTCTATG | CCCGGCCATT | TGGGCGTGCC | CCCGCAAGAC | 180 |
| TGCTAGCCGA | GTAG | | | | | 194 |